(12) United States Patent
Kasai et al.

(10) Patent No.: US 12,102,699 B2
(45) Date of Patent: Oct. 1, 2024

(54) FOAMING COMPOSITION COMPRISING OIL

(71) Applicant: L'OREAL, Paris (FR)

(72) Inventors: Takehiko Kasai, Kawasaki (JP);
Toshifumi Shiroya, Kawasaki (JP);
Shoji Maruyama, Kawasaki (JP);
Hidehiko Asanuma, Kawasaki (JP)

(73) Assignee: L'Oreal, Paris (FR)

( * ) Notice: Subject to any disclaimer, the term of this patent is extended or adjusted under 35 U.S.C. 154(b) by 719 days.

(21) Appl. No.: 17/271,158

(22) PCT Filed: Aug. 9, 2019

(86) PCT No.: PCT/JP2019/032208
§ 371 (c)(1),
(2) Date: Feb. 24, 2021

(87) PCT Pub. No.: WO2020/045135
PCT Pub. Date: Mar. 5, 2020

(65) Prior Publication Data
US 2021/0196583 A1    Jul. 1, 2021

(30) Foreign Application Priority Data
Aug. 30, 2018   (JP) ................. 2018-161328

(51) Int. Cl.
| | |
|---|---|
| *A61K 8/04* | (2006.01) |
| *A45D 34/00* | (2006.01) |
| *A61K 8/362* | (2006.01) |
| *A61K 8/55* | (2006.01) |
| *A61K 8/73* | (2006.01) |
| *A61Q 5/02* | (2006.01) |
| *A61Q 19/00* | (2006.01) |
| *B05B 7/00* | (2006.01) |

(52) U.S. Cl.
CPC .............. *A61K 8/046* (2013.01); *A45D 34/00* (2013.01); *A61K 8/362* (2013.01); *A61K 8/55* (2013.01); *A61K 8/731* (2013.01); *A61Q 5/02* (2013.01); *A61Q 19/00* (2013.01); *B05B 7/0018* (2013.01); *A45D 2200/056* (2013.01); *A61K 2800/87* (2013.01)

(58) Field of Classification Search
CPC ...................................................... A61K 8/046
See application file for complete search history.

(56) References Cited

U.S. PATENT DOCUMENTS

| 11,826,455 | B2 | 11/2023 | Shiroya et al. | |
|---|---|---|---|---|
| 2003/0022799 | A1* | 1/2003 | Alvarado | A61K 8/046 |
| | | | | 510/121 |
| 2004/0191199 | A1 | 9/2004 | Mougin | |
| 2004/0235693 | A1 | 11/2004 | Wei | |
| 2009/0175808 | A1 | 7/2009 | Galley | |
| 2013/0178508 | A1 | 7/2013 | Shirai | |
| 2013/0280174 | A1* | 10/2013 | Lipic | C11C 3/00 |
| | | | | 424/70.17 |
| 2014/0328938 | A1* | 11/2014 | Miller | C11D 1/667 |
| | | | | 424/535 |
| 2014/0335039 | A1 | 11/2014 | Merat | |
| 2015/0057461 | A1* | 2/2015 | Park | C12P 7/62 |
| | | | | 554/219 |
| 2015/0093348 | A1* | 4/2015 | Sato | A61K 8/046 |
| | | | | 424/70.19 |
| 2015/0272865 | A1 | 10/2015 | Mette | |
| 2017/0326041 | A1 | 11/2017 | Tsuzuki | |
| 2018/0344618 | A1 | 12/2018 | Motornov | |
| 2021/0177725 | A1 | 6/2021 | Shiroya et al. | |

FOREIGN PATENT DOCUMENTS

| AU | 2005241115 | B2 | 11/2005 | |
|---|---|---|---|---|
| AU | 2005241115 | * | 4/2011 | ........... C11D 3/3738 |
| CN | 1780600 | | 5/2006 | |
| CN | 101155842 | | 4/2008 | |
| CN | 103313699 | | 9/2013 | |
| CN | 108366915 | A | 8/2018 | |
| CN | 108367175 | A | 8/2018 | |
| DE | 102010029628 | | 12/2010 | |
| DE | 102012222771 | | 6/2014 | |
| EP | 0256691 | | 2/1988 | |
| EP | 1593371 | | 11/2005 | |
| EP | 2022480 | | 2/2009 | |
| EP | 2022482 | | 2/2009 | |

(Continued)

OTHER PUBLICATIONS

Office Action mailed Jun. 6, 2022, issued in related Japanese Application No. 2018-161328, 13 pages.
Whip Cream Shampoo (ID: 5765605), Mintel GNPD [online], Jun. 2018, [search date; May 23, 2022], Ingredients, Description of goods and Contents of appeal, <https://www.gnpd.com>, 5 pages.
Neo for Men 3x1 Multi-Functional Total Fresh Hair Body Beard Conditioning Shampoo (ID: 5083533), Mintel GNPD [online], Sep. 2017, [search date; May 23, 2022], Ingredients, Description of goods and Contents of appeal, <https://www.gnpd.com>, 4 pages.
Strengthening & Darkening Essence Oil Shampoo (ID: 3664321), Mintel GNPD [online], Dec. 2015, [search date; May 23, 2022], Ingredients, Description of goods and Contents of appeal, <https://www.gnpd.com>, 4 pages.

(Continued)

*Primary Examiner* — J C Jacyna
(74) *Attorney, Agent, or Firm* — CHRISTENSEN O'CONNOR JOHNSON KINDNESS PLLC

(57) ABSTRACT

The present invention relates to a foaming composition comprising: (a) at least one cationic polysaccharide; (b) at least one crosslinker having three or more acid groups or salt thereof; (c) at least one oil; and (d) at least one physiologically acceptable volatile medium, wherein the amount of the (c) oil(s) in the composition is 10% by weight or more, preferably 15% by weight or more, and more preferably 20% by weight or more, relative to the total weight of the composition. The composition according to the present invention can form a foam which is stable over time.

20 Claims, No Drawings

(56) References Cited

FOREIGN PATENT DOCUMENTS

| | | | |
|---|---|---|---|
| FR | 2881955 | A1 | 8/2006 |
| JP | 2006273855 | | 10/2006 |
| JP | 2010285432 | | 12/2010 |
| JP | 2016113405 | | 6/2016 |
| KR | 10-2014-0105728 | A | 9/2014 |
| WO | 2012038534 | A1 | 3/2012 |
| WO | 2013/069165 | A1 | 5/2013 |
| WO | 2016098786 | | 6/2016 |

OTHER PUBLICATIONS

First Office Action mailed Sep. 6, 2022, issued in related Chinese Application No. 201980055675.7, filed Aug. 9, 2019, 20 pages.
International Search Report mailed Dec. 2, 2019, issued in corresponding International Application No. PCT/JP2019/032208, filed Aug. 9, 2019, 2 pages.
Notice of Allowance mailed Jul. 24, 2023, issued in corresponding Chinese Application No. 201980052588.6, filed Aug. 16, 2019, 7 pages.
Wu, W., et al., "Principle and application of emulsion and foam systems stabilized by particles. . Application of particle—stabilized emulsions and foams," China Surfactant Detergent & Cosmetics, vol. 43, No. 6, Dec. 2013, pp. 418-423.
Notice of Allowance mailed Jul. 20, 2023, issued in corresponding Korean Application No. 10-2021-7003450, filed Aug. 16, 2019, 4 pages.
Huang, Y., et al., "Self-Assembly of Stiff, Adhesive and Self-Healing Gels from Common Polyelectrolytes," Langmuir, 2014, 30, 7771-7777.
"Peeling Mask", https://www.gnpd.com, Mintel, ID: 1868355, 2012, 3 pages (with partial translation).
"Purifying Toner", https://www.gnpd.com, Mintel, ID: 1007859, 2008 3 pages (with partial translation).
Taylor, D.L., et al., "Self-Healing Hydrogels," Advanced Materials, 2016, 28, 9060-9093.
Wang, S., "Chemistry of Daily Chemicals Formula Design and Production Process of Daily Chemicals," Harbin Institute of Technology Press, Aug. 31, 2001, pp. 129-130.
Zhong, P. et al., "Biochemicals Production Technology," Jiangxi Science & Technology Publishing House, May 31, 2007 pp. 335-336.
First Office Action mailed Sep. 7, 2022, issued in corresponding Chinese Application No. 201980055963.2, filed Aug. 9, 2019, 20 pages.
International Search Report mailed Dec. 2, 2019, issued in corresponding International Application No. PCT/JP2019/032207, filed Aug. 9, 2019, 3 pages.
Office Action mailed Jun. 6, 2022, issued in corresponding Japanese Application No. 2018-161327, filed on Aug. 30, 2018, 13 pages.
International Search Report mailed Nov. 20, 2019, issued in corresponding International Application PCT/JP2019/032929, filed Aug. 16, 2019, 3 pages.
Notice of Reasons for Refusal mailed Jun. 6, 2022, issued in corresponding Japanese Application No. 2018-161330, 10 pages.
First Chinese Office Action mailed Sep. 29, 2022, issued in corresponding Chinese Application No. 201980052588.6, filed Aug. 16, 2019, 17 pages.
Second Office Action mailed Jan. 28, 2023, issued in corresponding Chinese Application No. 201980055963.2, filed Aug. 9, 2019, 18 pages.
Database GNPD [Online], Mintel; May 29, 2015 (May 29, 2015), anonymous: "Double Header Shampoo + Conditioner", XP055627712, Database accession No. 3553211 (3 pages).
Office Action for EP 19763113.8, mailed Sep. 13, 2023.

* cited by examiner

FOAMING COMPOSITION COMPRISING OIL

TECHNICAL FIELD

The present invention relates to a foam including a dynamically and ionically-crosslinked (DIC) gel and oil.

BACKGROUND ART

Foams have been applied to a variety of cosmetics such as shampoos, cleansers and hair treatments. Foams are preferable in terms of, for example, handling, because dripping off of cosmetics through the fingers can be prevented or reduced.

Recently, there is a need to prepare foams which can include a substantial amount of oil. For instance, it may be preferable for a hair conditioner which can provide hair with cosmetic effects under wet and dry conditions to form foams including a substantial amount of oil for hair manageability and the like.

However, it is difficult to include a substantial amount of oil in a foam because oils can function as a defoamer. Thus, a foam including a substantial amount of oil tends to be unstable or easily breaks the bubble structures in the foam.

DISCLOSURE OF INVENTION

Thus, the objective of the present invention is to provide a composition which can form a stable foam even though the composition includes a substantial amount of oil.

The above objective of the present invention can be achieved by a foaming composition comprising:
(a) at least one cationic polysaccharide;
(b) at least one crosslinker having three or more acid groups or salt thereof;
(c) at least one oil; and
(d) at least one physiologically acceptable volatile medium,
wherein
the amount of the (c) oil(s) in the composition is 10% by weight or more, preferably 15% by weight or more, and more preferably 20% by weight or more, relative to the total weight of the composition.

The (a) cationic polysaccharide may be selected from cationic cellulose polymers.

The (a) cationic polysaccharide may have at least one quaternary ammonium group.

The (a) cationic polysaccharide may be selected from the group consisting of polyquaternium-4, polyquaternium-10, polyquaternium-24, polyquaternium-67, and a mixture thereof.

The amount of the (a) cationic polysaccharide(s) in the composition according to the present invention may be from 0.01% to 20% by weight, preferably from 0.1% to 15% by weight, and more preferably from 0.5% to 10% by weight, relative to the total weight of the composition.

The (b) crosslinker having three or more acid groups or salt thereof may be selected from non-polymeric organic acids having three or more acid groups and salts thereof.

The (b) crosslinker having three or more acid groups may have three or more acid groups selected from the group consisting of a carboxylic group, a sulfuric group, a sulfonic group, a phosphonic group, phosphoric group, a phenolic hydroxyl group, and a mixture thereof.

The (b) crosslinker having three or more acid groups or salt thereof may be selected from the group consisting of phytic acid, citric acid, aconitic acid, EDTA, glycyrrhizin, inositol triphosphate, inositol pentakisphosphate, tripolyphosphate, adenosine triphosphate, a salt thereof, and a mixture thereof.

The amount of the (b) crosslinker(s) having three or more acid groups or salt(s) thereof in the composition according to the present invention may be from 0.001% to 15% by weight, preferably from 0.05% to 10% by weight, and more preferably from 0.1% to 5% by weight, relative to the total weight of the composition.

The amount of the (c) oil(s) in the composition according to the present invention may be less than 50% by weight, preferably less than 45% by weight, and more preferably less than 40% by weight, relative to the total weight of the composition.

The amount of the (d) physiologically acceptable volatile medium(s), preferably water, in the composition according to the present invention may be from 50% to 90% by weight, preferably from 55% to 85% by weight, and more preferably from 60% to 80% by weight, relative to the total weight of the composition.

The composition according to the present invention may further comprise (e) at least one anionic polymer.

The composition according to the present invention may be a cosmetic composition, preferably a skin cosmetic composition.

The composition according to the present invention may further comprise at least one gas and may be in the form of a foam.

The present invention also relates to a cosmetic process for a keratin substance such as skin, comprising the steps of:
foaming the composition according to the present invention; and
applying the foam to the keratin substrate.

The present invention also relates to a foaming product comprising:
at least one container comprising the composition according to any one of claims 1 to 13; and
at least one dispenser,
wherein
the dispenser is capable of discharging the composition in the form of a foam.

The container may further comprise at least one propellant.

The foaming product according to the present invention may further comprise at least one pump which is connected to the container and the dispenser, wherein the pump is capable of mixing the composition with at least one gas to prepare a foam and of conveying the foam to the dispenser.

BEST MODE FOR CARRYING OUT THE INVENTION

After diligent research, the inventors have discovered that it is possible to provide a composition which can form a stable foam even though the composition includes a substantial amount of oil. Thus, the composition according to the present invention comprises:
(a) at least one cationic polysaccharide;
(b) at least one crosslinker having three or more acid groups or salt thereof;
(c) at least one oil; and
(d) at least one physiologically acceptable volatile medium,
wherein
the amount of the (c) oil(s) in the composition is 10% by weight or more, preferably 15% by weight or more, and more preferably 20% by weight or more, relative to the total weight of the composition.

The composition according to the present invention is a foaming composition. In other words, the composition according to the present invention is capable of forming a foam. The composition according to the present invention can form a foam which is stable over time or for a long period of time, e.g., more than a few minutes, preferably 10 minutes or more, and more preferably 20 minutes or more.

The composition according to the present invention can prepare a gel, preferably a hydrogel. The gel is dynamically and ionically-crosslinked. The dynamically and ionically-crosslinked gel prepared by the composition according to the present invention is abbreviated as a DIC-gel.

The dynamic and ionic-crosslinking in the DIC-gel is different from permanent covalent bonding because it is breakable but reformable. The dynamic and ionic-crosslinking can be easily broken by, for example, cutting and the like, but can be easily reformed by, for example, contacting each other. For example, if the gel is cut into two pieces, the ionic interaction between the cationic polymer and the crosslinker breaks. However, if the two pieces contact each other, they can reform ionic-bonding between the cationic polymer and the crosslinker, and they can adhere to each other. Therefore, even if cracks, for example, are formed on the gel, they can disappear.

The gel prepared by the (a) cationic polysaccharide and the (b) crosslinker having three or more acid groups or salt thereof can form a film Without wishing to be bound by any theory, it is assumed that the film will be present at the surface of bubbles in a foam to stabilize the foam. Therefore, even if a substantial amount of oil which can function as a defoamer, such as silicone, is present, the foam formed by the composition according to the present invention can be maintained, and therefore the foam is stable.

Also, the composition according to the present invention can provide superior cosmetic effects, e.g., conditioning effects for keratin fibers such as hair. For example, keratin fibers treated with the composition according to the present invention can be smoother.

It is preferable that the composition according to the present invention be substantially free from surfactants which are conventionally used to form a foam because surfactants have several concerns such as tacky texture, skin irritation and environment load. Even without any surfactant, the composition according to the present invention can prepare a stable foam.

Hereinafter, the composition, process and the like according to the present invention will be explained in a more detailed manner.

(Cationic Polysaccharide)

The composition according to the present invention includes (a) at least one cationic polysaccharide. Two or more different types of (a) cationic polysaccharides may be used in combination. Thus, a single type of (a) cationic polysaccharide or a combination of different types of (a) cationic polysaccharides may be used.

The (a) cationic polysaccharide has a positive charge density. The charge density of the (a) cationic polysaccharide may be from 0.01 meq/g to 20 meq/g, preferably from 0.05 to 15 meq/g, and more preferably from 0.1 to 10 meq/g.

It may be preferable that the molecular weight of the (a) cationic polysaccharide be 500 or more, preferably 1,000 or more, more preferably 2,000 or more, and even more preferably 5,000 or more.

Unless otherwise defined in the description, "molecular weight" means a number average molecular weight.

The (a) cationic polysaccharide may have at least one positively chargeable and/or positively charged moiety selected from the group consisting of a primary, a secondary or tertiary amino group, a quaternary ammonium group, a guanidine group, a biguanide group, an imidazole group, an imino group, and a pyridyl group. The term (primary) "amino group" here means the group —$NH_2$. It is preferable that the (a) cationic polysaccharide have at least one quaternary ammonium group.

The (a) cationic polysaccharide may be a homopolymer or a copolymer. The term "copolymer" is understood to mean both copolymers obtained from two kinds of monomers and those obtained from more than two kinds of monomers, such as terpolymers obtained from three kinds of monomers.

The (a) cationic polysaccharide may be selected from natural and synthetic cationic polysaccharides.

It is preferable that the (a) cationic polysaccharide be selected from cationic cellulose polymers. Non-limiting examples of the cationic cellulose polymers are as follows.

(1) Cationic cellulose polymers such as cellulose ether derivatives comprising one or more quaternary ammonium groups described, for example, in French Patent No. 1 492 597, such as the polymers sold under the names "JR" (JR 400, JR 125, JR 30M) or "LR" (LR 400, LR 30M) by the company Dow Chemical. These polymers are also defined in the CTFA dictionary as quaternary ammoniums of hydroxyethylcellulose that have reacted with an epoxide substituted with a trimethylammonium group.

(2) Cationic cellulose polymers such as cellulose copolymers and cellulose derivatives grafted with at least one water-soluble monomer of quaternary ammonium, and described, for example, in U.S. Pat. No. 4,131,576, such as hydroxyalkylcelluloses, for instance, hydroxymethyl-, hydroxyethyl-, and hydroxypropyl-celluloses grafted, for example, with at least one chosen from methacryloylethyltrimethylammonium, methacrylamidopropyltrimethylammonium, and dimethyldiallylammonium. Commercial products corresponding to these polymers include, for example, the products sold under the names "Celquat® L 200" and "Celquat® H 100" by the company Akzo Novel.

(3) Cationic cellulose polymers having at least one quaternary ammonium group comprising at least one fatty chain, such as alkyl, arylalkyl or alkylaryl groups comprising at least 8 carbon atoms. It may be preferable that the cationic cellulose polymers be quaternized hydroxyethylcelluloses modified with at least one quaternary ammonium group comprising at least one fatty chain, such as alkyl, arylalkyl or alkylaryl groups comprising at least 8 carbon atoms, or mixtures thereof. The alkyl radicals borne by the quaternary ammonium group may preferably contain from 8 to 30 carbon atoms, especially from 10 to 30 carbon atoms. The aryl radicals preferably denote phenyl, benzyl, naphthyl or anthryl groups. More preferably, the cationic cellulose polymer may comprise at least one quaternary ammonium group including at least one $C_8$-$C_{30}$ hydrocarbon group. Examples of quaternized alkylhydroxyethylcelluloses containing $C_8$-$C_{30}$ fatty chains that may be mentioned include the products Quatrisoft LM 200, Quatrisoft LM-X 529-18-A, Quatrisoft LM-X 529-18B (C12 alkyl) and Quatrisoft LM-X 529-8 (C18 alkyl) or Softcat Polymer SL100, Softcat SX-1300X, Softcat SX-1300H, Softcat SL-5, Softcat SL-30, Softcat SL-60, Softcat SK-MH, Softcat SX-400X, Softcat SX-400H, SoftCat SK-L, Softcat SK-M, and Softcat SK-H, sold by the company Dow Chemical, and the products Crodacel QM, Crodacel, QL (C12 alkyl) and Crodacel QS ($C_{18}$ alkyl) sold by the company Croda.

It is preferable that the (a) cationic polysaccharide be selected from the group consisting of polyquaternium-4, polyquaternium-10, polyquaternium-24, polyquaternium-67, and a mixture thereof.

Without wishing to be bound by any theory, it is assumed that the semi-flexibility or the relatively rigid polymer structure of the (a) cationic polysaccharide might contribute to stable foam including a substantial amount of oil. Also, it should be noted that the semi-flexibility or the relatively rigid polymer structure of the (a) cationic polysaccharide is advantageous to make micro-gels.

The amount of the (a) cationic polysaccharide(s) in the composition according to the present invention may be 0.01% by weight or more, preferably 0.1% by weight or more, and more preferably 0.5% by weight or more, relative to the total weight of the composition.

The amount of the (a) cationic polysaccharide(s) in the composition according to the present invention may be 20% by weight or less, preferably 15% by weight or less, and more preferably 10% by weight or less, relative to the total weight of the composition.

The amount of the (a) cationic polysaccharide(s) in the composition according to the present invention may be from 0.01% to 20% by weight, preferably from 0.1% to 15% by weight, and more preferably from 0.5% to 10% by weight, relative to the total weight of the composition.

(Crosslinker)

The composition according to the present invention includes (b) at least one crosslinker having three or more acid groups or salt thereof. Two or more different types of (b) crosslinkers or salts thereof may be used in combination. Thus, a single type of (b) crosslinker or salt thereof or a combination of different types of (b) crosslinkers or salts thereof may be used.

At least one of the acid groups of the (b) crosslinker having three or more acid groups may be in the form of a salt. All the acid groups of the (b) crosslinker may be in the form of salts.

The term "salt" in the present specification means a salt formed by addition of suitable base(s) to the (b) crosslinker having three or more acid groups, which may be obtained from a reaction with the (b) crosslinker having three or more acid groups with the base(s) according to the methods known to those skilled in the art. As the salt, mention may be made of metal salts, for example salts with alkaline metal such as Na and Ka, and salts with alkaline earth metal such as Mg and Ca, and ammonium salts.

It is preferable that the (b) crosslinker be selected from non-polymeric acids having three or more acid groups, more preferably from non-polymeric organic acids having three or more acid groups.

The term "non-polymeric" here means that the (b) crosslinker is not obtained by polymerizing two or more monomers. Therefore, the non-polymeric acid, in particular the non-polymeric organic acid, does not correspond to an acid obtained by polymerizing two or more monomers such as polycarboxylic acid.

It is preferable that the molecular weight of the non-polymeric acid, in particular the non-polymeric organic acid, having three or more acid groups be 1000 or less, preferably 800 or less, and more preferably 600 or less.

The (b) crosslinker having three or more acid groups, or salt thereof, may be hydrophilic or water-soluble.

The (b) crosslinker having three or more acid groups may have three or more acid groups selected from the group consisting of a carboxylic group, a sulfuric group, a sulfonic group, a phosphonic group, phosphoric group, a phenolic hydroxyl group, and a mixture thereof.

The (b) crosslinker having three or more acid groups or salt thereof may be selected from the group consisting of tricarboxylic acids, tetracarboxylic acids, pentacarboxylic acids, hexacarboxylic acids, salts thereof, and mixtures thereof.

The (b) crosslinker having three or more acid groups or salt thereof may be selected from the group consisting of citric acid, aconitic acid, phytic acid, EDTA, glycyrrhizin, inositol triphosphate, inositol pentakisphosphate, tripolyphosphate, adenosine triphosphate, a salt thereof, and a mixture thereof.

It may be preferable that the (b) crosslinker having three or more acid groups or salt thereof be selected from the group consisting of citric acid, phytic acid, a salt thereof, and a mixture thereof.

Without wishing to be bound by any theory, it is assumed that the dynamic and ionic crosslinking by a crosslinker having three or more acid groups such as phytic acid could make a robust interfacial film around bubbles in the foam which would contribute to the stability of foams.

The amount of the (b) crosslinker(s) having three or more acid groups or salt(s) thereof in the composition according to the present invention may be 0.001% by weight or more, preferably 0.05% by weight or more, and more preferably 0.1% by weight or more, relative to the total weight of the composition.

The amount of the (b) crosslinker(s) having three or more acid groups or salt(s) thereof in the composition according to the present invention may be 15% by weight or less, preferably 10% by weight or less, and more preferably 5% by weight or less, relative to the total weight of the composition.

The amount of the (b) crosslinker(s) having three or more acid groups or salt(s) thereof in the composition according to the present invention may be from 0.001% to 15% by weight, preferably from 0.05% to 10% by weight, and more preferably from 0.1% to 5% by weight, relative to the total weight of the composition.

(Oil)

The composition according to the present invention comprises (c) at least one oil. If two or more (c) oils are used, they may be the same or different.

Here, "oil" means a fatty compound or substance which is in the form of a liquid or a paste (non-solid) at room temperature (25° C.) under atmospheric pressure (1 atm). As the oils, those generally used in cosmetics can be used alone or in combination thereof. These oils may be volatile or non-volatile.

The oil may be a non-polar oil such as a hydrocarbon oil, a silicone oil, or the like; a polar oil such as a plant or animal oil and an ester oil or an ether oil; or a mixture thereof.

The oil may be selected from the group consisting of oils of plant or animal origin, synthetic oils, silicone oils, hydrocarbon oils and fatty alcohols.

As examples of plant oils, mention may be made of, for example, linseed oil, *camellia* oil, macadamia nut oil, corn oil, mink oil, olive oil, avocado oil, sasanqua oil, castor oil, safflower oil, jojoba oil, sunflower oil, almond oil, rapeseed oil, sesame oil, soybean oil, peanut oil, and mixtures thereof.

As examples of animal oils, mention may be made of, for example, squalene and squalane.

As examples of synthetic oils, mention may be made of alkane oils such as isododecane and isohexadecane, ester oils, ether oils, and artificial triglycerides.

The ester oils are preferably liquid esters of saturated or unsaturated, linear or branched $C_1$-$C_{26}$ aliphatic monoacids or polyacids and of saturated or unsaturated, linear or branched $C_1$-$C_{26}$ aliphatic monoalcohols or polyalcohols, the total number of carbon atoms of the esters being greater than or equal to 10.

Preferably, for the esters of monoalcohols, at least one from among the alcohol and the acid from which the esters of the present invention are derived is branched.

Among the monoesters of monoacids and of monoalcohols, mention may be made of ethyl palmitate, ethyl hexyl palmitate, isopropyl palmitate, dicaprylyl carbonate, alkyl myristates such as isopropyl myristate or ethyl myristate, isocetyl stearate, 2-ethylhexyl isononanoate, isononyl isononanoate, isodecyl neopentanoate and isostearyl neopentanoate.

Esters of $C_4$-$C_{22}$ dicarboxylic or tricarboxylic acids and of $C_1$-$C_{22}$ alcohols, and esters of monocarboxylic, dicarboxylic or tricarboxylic acids and of non-sugar $C_4$-$C_{26}$ dihydroxy, trihydroxy, tetrahydroxy or pentahydroxy alcohols may also be used.

Mention may especially be made of: diethyl sebacate; isopropyl lauroyl sarcosinate; diisopropyl sebacate; bis(2-ethylhexyl) sebacate; diisopropyl adipate; di-n-propyl adipate; dioctyl adipate; bis(2-ethylhexyl) adipate; diisostearyl adipate; bis(2-ethylhexyl) maleate; triisopropyl citrate; triisocetyl citrate; triisostearyl citrate; glyceryl trilactate; glyceryl trioctanoate; trioctyldodecyl citrate; trioleyl citrate; neopentyl glycol diheptanoate; diethylene glycol diisononanoate.

As ester oils, one can use sugar esters and diesters of $C_6$-$C_{30}$ and preferably $C_{12}$-$C_{22}$ fatty acids. It is recalled that the term "sugar" means oxygen-bearing hydrocarbon-based compounds containing several alcohol functions, with or without aldehyde or ketone functions, and which comprise at least 4 carbon atoms. These sugars may be monosaccharides, oligosaccharides or polysaccharides.

Examples of suitable sugars that may be mentioned include sucrose (or saccharose), glucose, galactose, ribose, fucose, maltose, fructose, mannose, arabinose, xylose and lactose, and derivatives thereof, especially alkyl derivatives, such as methyl derivatives, for instance methylglucose.

The sugar esters of fatty acids may be chosen especially from the group comprising the esters or mixtures of esters of sugars described previously and of linear or branched, saturated or unsaturated $C_6$-$C_{30}$ and preferably $C_{12}$-$C_{22}$ fatty acids. If they are unsaturated, these compounds may have one to three conjugated or non-conjugated carbon-carbon double bonds.

The esters according to this variant may also be selected from monoesters, diesters, triesters, tetraesters and polyesters, and mixtures thereof.

These esters may be, for example, oleates, laurates, palmitates, myristates, behenates, cocoates, stearates, linoleates, linolenates, caprates and arachidonates, or mixtures thereof such as, especially, oleopalmitate, oleostearate and palmitostearate mixed esters, as well as pentaerythrityl tetraethyl hexanoate.

More particularly, use is made of monoesters and diesters and especially sucrose, glucose or methylglucose monooleates or dioleates, stearates, behenates, oleopalmitates, linoleates, linolenates and oleostearates.

An example that may be mentioned is the product sold under the name Glucate® DO by the company Amerchol, which is a methylglucose dioleate.

As examples of preferable ester oils, mention may be made of, for example, diisopropyl adipate, dioctyl adipate, 2-ethylhexyl hexanoate, ethyl laurate, cetyl octanoate, octyldodecyl octanoate, octyldodecyl myristate, isodecyl neopentanoate, myristyl propionate, 2-ethylhexyl 2-ethylhexanoate, 2-ethylhexyl octanoate, 2-ethylhexyl caprylate/caprate, methyl palmitate, ethyl palmitate, isopropyl palmitate, dicaprylyl carbonate, isopropyl lauroyl sarcosinate, isononyl isononanoate, ethylhexyl palmitate, isohexyl laurate, hexyl laurate, isocetyl stearate, isopropyl isostearate, isopropyl myristate, isodecyl oleate, glyceryl tri(2-ethylhexanoate), pentaerythrityl tetra(2-ethylhexanoate), 2-ethylhexyl succinate, diethyl sebacate, and mixtures thereof.

As examples of artificial triglycerides, mention may be made of, for example, capryl caprylyl glycerides, glyceryl trimyristate, glyceryl tripalmitate, glyceryl trilinolenate, glyceryl trilaurate, glyceryl tricaprate, glyceryl tricaprylate, glyceryl tri(caprate/caprylate) and glyceryl tri(caprate/caprylate/linolenate).

As examples of silicone oils, mention may be made of, for example, linear organopolysiloxanes such as dimethylpolysiloxane, methylphenylpolysiloxane, methylhydrogenpolysiloxane, and the like; cyclic organopolysiloxanes such as octamethylcyclotetrasiloxane, decamethylcyclopentasiloxane, dodecamethylcyclohexasiloxane, and the like; and mixtures thereof.

Preferably, silicone oil is chosen from liquid polydialkylsiloxanes, especially liquid polydimethylsiloxanes (PDMS) and liquid polyorganosiloxanes comprising at least one aryl group.

These silicone oils may also be organomodified. The organomodified silicones that can be used according to the present invention are silicone oils as defined above and comprise in their structure one or more organofunctional groups attached via a hydrocarbon-based group.

Organopolysiloxanes are defined in greater detail in Walter Noll's *Chemistry and Technology of Silicones* (1968), Academic Press. They may be volatile or non-volatile.

When they are volatile, the silicones are more particularly chosen from those having a boiling point of between 60° C. and 260° C., and even more particularly from:

(i) cyclic polydialkylsiloxanes comprising from 3 to 7 and preferably 4 to 5 silicon atoms. These are, for example, octamethylcyclotetrasiloxane sold in particular under the name Volatile Silicone® 7207 by Union Carbide or Silbione® 70045 V2 by Rhodia, decamethylcyclopentasiloxane sold under the name Volatile Silicone® 7158 by Union Carbide, Silbione® 70045 V5 by Rhodia, and dodecamethylcyclopentasiloxane sold under the name Silsoft 1217 by Momentive Performance Materials, and mixtures thereof. Mention may also be made of cyclocopolymers of the type such as dimethylsiloxane/methylalkylsiloxane, such as Silicone Volatile® FZ 3109 sold by the company Union Carbide, of formula:

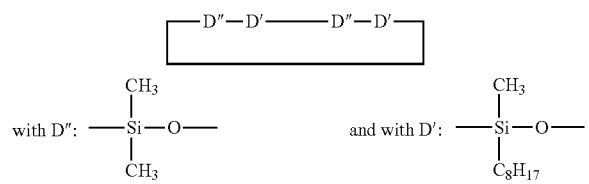

Mention may also be made of mixtures of cyclic polydialkylsiloxanes with organosilicon compounds, such as the mixture of octamethylcyclotetrasiloxane and tetratrimethylsilylpentaerythritol (50/50) and the mixture of octamethylcyclotetrasiloxane and oxy-1,1'-bis(2,2,2',2',3,3'-hexatrimethylsilyloxy)neopentane; and (ii) linear volatile polydialkylsiloxanes containing 2 to 9 silicon atoms and having a viscosity of less than or equal to $5\times10^{-6}$ m$^2$/s at 25° C. An example is decamethyltetrasiloxane sold in particular under the name SH 200 by the company Toray Silicone. Silicones belonging to this category are also described in the article published in Cosmetics and Toiletries, Vol. 91, January 76, pp. 27-32, Todd & Byers, *Volatile Silicone Fluids for Cosmetics*. The viscosity of the silicones is measured at 25° C. according to ASTM standard 445 Appendix C.

Non-volatile polydialkylsiloxanes may also be used. These non-volatile silicones are more particularly chosen from polydialkylsiloxanes, among which mention may be made mainly of polydimethylsiloxanes containing trimethylsilyl end groups.

Among these polydialkylsiloxanes, mention may be made, in a non-limiting manner, of the following commercial products:
  the Silbione® oils of the 47 and 70 047 series or the Mirasil® oils sold by Rhodia, for instance the oil 70 047 V 500 000;
  the oils of the Mirasil® series sold by the company Rhodia;
  the oils of the 200 series from the company Dow Corning, such as DC200 with a viscosity of 60 000 mm$^2$/s; and
  the Viscasil® oils from General Electric and certain oils of the SF series (SF 96, SF 18) from General Electric.

Mention may also be made of polydimethylsiloxanes containing dimethylsilanol end groups known under the name dimethiconol (CTFA), such as the oils of the 48 series from the company Rhodia.

Among the silicones containing aryl groups, mention may be made of polydiarylsiloxanes, especially polydiphenylsiloxanes and polyalkylarylsiloxanes such as phenyl silicone oil.

The phenyl silicone oil may be chosen from the phenyl silicones of the following formula:

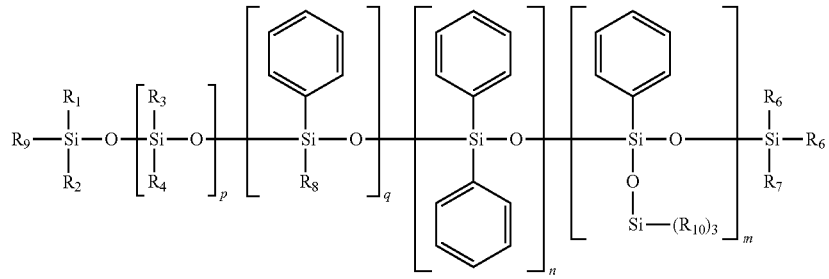

in which
  $R_1$ to $R_{10}$, independently of each other, are saturated or unsaturated, linear, cyclic or branched $C_1$-$C_{30}$ hydrocarbon-based radicals, preferably $C_1$-$C_{12}$ hydrocarbon-based radicals, and more preferably $C_1$-$C_6$ hydrocarbon-based radicals, in particular methyl, ethyl, propyl or butyl radicals, and m, n, p and q are, independently of each other, integers 0 to 900 inclusive, preferably 0 to 500 inclusive, and more preferably 0 to 100 inclusive, with the proviso that the sum n+m+q is other than 0.

Examples that may be mentioned include the products sold under the following names:
  the Silbione® oils of the 70 641 series from Rhodia;
  the oils of the Rhodorsil® 70 633 and 763 series from Rhodia;
  the oil Dow Corning 556 Cosmetic Grade Fluid from Dow Corning;
  l the silicones of the PK series from Bayer, such as the product PK20;
  certain oils of the SF series from General Electric, such as SF 1023, SF 1154, SF 1250 and SF 1265.

As the phenyl silicone oil, phenyl trimethicone ($R_1$ to $R_{10}$ are methyl; p, q, and n=0; m=1 in the above formula) is preferable.

The organomodified liquid silicones may especially contain polyethyleneoxy and/or polypropyleneoxy groups. Mention may thus be made of the silicone KF-6017 proposed by Shin-Etsu, and the oils Silwet® L722 and L77 from the company Union Carbide.

Hydrocarbon oils may be chosen from:
  linear or branched, optionally cyclic, $C_6$-$C_{16}$ lower alkanes. Examples that may be mentioned include hexane, undecane, dodecane, tridecane, and isoparaffins, for instance isohexadecane, isododecane and isodecane; and
  linear or branched hydrocarbons containing more than 16 carbon atoms, such as liquid paraffins, liquid petroleum jelly, polydecenes and hydrogenated polyisobutenes such as Parleam®, and squalane.

As preferable examples of hydrocarbon oils, mention may be made of, for example, linear or branched hydrocarbons such as isohexadecane, isododecane, squalane, mineral oil (e.g., liquid paraffin), paraffin, vaseline or petrolatum, naphthalenes, and the like; hydrogenated polyisobutene, isoeicosan, and decene/butene copolymer; and mixtures thereof.

The term "fatty" in the fatty alcohol means the inclusion of a relatively large number of carbon atoms. Thus, alcohols which have 4 or more, preferably 6 or more, and more preferably 12 or more carbon atoms are encompassed within the scope of fatty alcohols. The fatty alcohol may be saturated or unsaturated. The fatty alcohol may be linear or branched.

The fatty alcohol may have the structure R—OH wherein R is chosen from saturated and unsaturated, linear and branched radicals containing from 4 to 40 carbon atoms, preferably from 6 to 30 carbon atoms, and more preferably from 12 to 20 carbon atoms. In at least one embodiment, R may be chosen from $C_{12}$-$C_{20}$ alkyl and $C_{12}$-$C_{20}$ alkenyl groups. R may or may not be substituted with at least one hydroxyl group.

As examples of the fatty alcohol, mention may be made of lauryl alcohol, cetyl alcohol, stearyl alcohol, isostearyl alcohol, behenyl alcohol, undecylenyl alcohol, myristyl alcohol, octyldodecanol, hexyldecanol, oleyl alcohol, linoleyl alcohol, palmitoleyl alcohol, arachidonyl alcohol, erucyl alcohol, and mixtures thereof.

It is preferable that the fatty alcohol be a saturated fatty alcohol.

Thus, the fatty alcohol may be selected from straight or branched, saturated or unsaturated $C_6$-$C_{30}$ alcohols, preferably straight or branched, saturated $C_6$-$C_{30}$ alcohols, and more preferably straight or branched, saturated $C_{12}$-$C_{20}$ alcohols.

The term "saturated fatty alcohol" here means an alcohol having a long aliphatic saturated carbon chain. It is preferable that the saturated fatty alcohol be selected from any linear or branched, saturated $C_6$-$C_{30}$ fatty alcohols. Among the linear or branched, saturated $C_6$-$C_{30}$ fatty alcohols, linear or branched, saturated $C_{12}$-$C_{20}$ fatty alcohols may preferably be used. Any linear or branched, saturated $C_{16}$-$C_{20}$ fatty alcohols may be more preferably used. Branched $C_{16}$-$C_{20}$ fatty alcohols may be even more preferably used.

As examples of saturated fatty alcohols, mention may be made of lauryl alcohol, cetyl alcohol, stearyl alcohol, isostearyl alcohol, behenyl alcohol, undecylenyl alcohol, myristyl alcohol, octyldodecanol, hexyldecanol, and mixtures thereof. In one embodiment, cetyl alcohol, stearyl alcohol, octyldodecanol, hexyldecanol, or a mixture thereof (e.g., cetearyl alcohol) as well as behenyl alcohol, can be used as a saturated fatty alcohol.

According to at least one embodiment, the fatty alcohol used in the composition according to the present invention is preferably chosen from octyldodecanol, hexyldecanol and mixtures thereof.

It may be preferable that the (c) oil be chosen from nonpolar oils, more preferably from silicone oils, hydrocarbon oils, and mixtures thereof, even more preferably silicone oils, and in particular volatile silicone oils.

The amount of the (c) oil(s) in the composition according to the present invention is 10% by weight or more, preferably 15% by weight or more, and more preferably 20% by weight or more, relative to the total weight of the composition. The amount of the (c) oil(s) in the composition according to the present invention may be 25% by weight or more or 30% by weight or more, relative to the total weight of the composition.

The amount of the (c) oil(s) in the composition according to the present invention may be less than 50% by weight, preferably less than 45% by weight, and more preferably less than 40% by weight, relative to the total weight of the composition.

The amount of the (c) oil(s) in the composition according to the present invention may be from 10% to less than 50% by weight, preferably from 15% to less than 45% by weight, and more preferably from 20% to less than 40% by weight, relative to the total weight of the composition.

(Physiologically Acceptable Volatile Medium)

The composition according to the present invention includes (d) at least one physiologically acceptable volatile medium.

The term "physiologically acceptable" volatile medium is intended to denote a volatile medium that is particularly suitable for applying the composition according to the present invention to keratin substance(s).

The term "volatile" means that the (d) physiologically acceptable medium can evaporate under a normal atmospheric pressure such as 1 atm and at room temperature such as 25° C.

The physiologically acceptable medium is generally adapted to the nature of the support onto which the composition according to the present invention is to be applied, and also to the form in which the composition according to the present invention is to be packaged.

The (d) physiologically acceptable volatile medium may comprise at least one hydrophilic organic solvent, water or a mixture thereof. It is preferable that the (d) physiologically acceptable volatile medium comprise water.

As the hydrophilic organic solvent, mention may be made of, for example, monoalcohols containing from 2 to 6 carbon atoms, such as ethanol or isopropanol; polyols especially containing from 2 to 20 carbon atoms, preferably containing from 2 to 10 carbon atoms and preferentially containing from 2 to 8 carbon atoms, such as glycerol, propylene glycol, butylene glycol, pentylene glycol, hexylene glycol, caprylyl glycol, dipropylene glycol or diethylene glycol; glycol ethers (especially containing from 3 to 16 carbon atoms) such as mono-, di- or tripropylene glycol ($C_1$-$C_4$) alkyl ethers, mono-, di- or triethylene glycol ($C_1$-$C_4$)alkyl ethers, and mixtures thereof.

The amount of the (d) physiologically acceptable volatile medium, preferably water, in the composition according to the present invention may be 50% by weight or more, preferably 55% by weight or more, and more preferably 60% by weight or more, relative to the total weight of the composition.

The amount of the (d) physiologically acceptable volatile medium, preferably water, in the composition according to the present invention may be 90% by weight or less, preferably 85% by weight or less, and more preferably 80% by weight or less, relative to the total weight of the composition.

The amount of the (d) physiologically acceptable volatile medium, preferably water, in the composition according to the present invention may be from 50% to 90% by weight, preferably from 55% to 85% by weight, and more preferably from 60% to 80% by weight, relative to the total weight of the composition.

(Anionic Polymer)

The composition according to the present invention may include (e) at least one anionic polymer. Two or more different types of (e) anionic polymers may be used in combination. Thus, a single type of (e) anionic polymer or a combination of different types of (d) anionic polymers may be used.

An anionic polymer has a negative charge density. The charge density of the anionic polymer may be from 0.1 meq/g to 20 meq/g, preferably from 1 to 15 meq/g, and more preferably from 4 to 10 meq/g if the anionic polymer is a synthetic anionic polymer, and the average substitution degree of the anionic polymer may be from 0.1 to 3.0, preferably from 0.2 to 2.7, and more preferably from 0.3 to 2.5 if the anionic polymer is a natural anionic polymer.

It may be preferable that the molecular weight of the anionic polymer be 1,000 or more, preferably 10,000 or more, more preferably 100,000 or more, and even more preferably 1,000,000 or more.

The anionic polymer may have at least one negatively chargeable and/or negatively charged moiety selected from the group consisting of a sulfuric group, a sulfate group, a sulfonic group, a sulfonate group, a phosphoric group, a phosphate group, a phosphonic group, phosphoric group, a phosphonate group, a carboxylic group, and a carboxylate group.

The anionic polymer may be a homopolymer or a copolymer. The term "copolymer" is understood to mean both copolymers obtained from two kinds of monomers and those obtained from more than two kinds of monomers, such as terpolymers obtained from three kinds of monomers.

The anionic polymer may be selected from natural and synthetic anionic polymers.

The anionic polymer may comprise at least one hydrophobic chain.

The anionic polymer which may comprise at least one hydrophobic chain may be obtained by copolymerization of a monomer (a) chosen from carboxylic acids comprising α,β-ethylenic unsaturation (monomer a') and 2-acrylamido-2-methylpropanesulphonic acid (monomer a") with a non-surface-active monomer (b) comprising ethylenic unsaturation other than (a) and/or a monomer (c) comprising ethylenic unsaturation resulting from the reaction of an acrylic monomer comprising α,β-monoethylenic unsaturation or of an isocyanate monomer comprising monoethylenic unsaturation with a monohydric nonionic amphiphilic component or with a primary or secondary fatty amine.

Thus, the anionic polymer with at least one hydrophobic chain may be obtained by two synthetic routes:
  either by copolymerization of the monomers (a') and (c), or (a'), (b) and (c), or (a") and (c), or (a"), (b) and (c),
  or by modification (and in particular esterification or amidation) of a copolymer formed from the monomers (a') or from the monomers (a') and (b), or (a") and (b), by a monohydric nonionic amphiphilic compound or a primary or secondary fatty amine.

Mention may in particular be made, as 2-acrylamido-2-methylpropanesulphonic acid copolymers, of those disclosed in the article "Micelle formation of random copolymers of sodium 2-(acrylamido)-2-methylpropanesulfonate and nonionic surfactant macromonomer in water as studied by fluorescence and dynamic light scattering—Macromolecules, 2000, Vol. 33, No. 10-3694-3704" and in applications EP-A-0 750 899 and EP-A-1 069 172.

The carboxylic acid comprising α,β-monoethylenic unsaturation constituting the monomer (a') can be chosen from numerous acids and in particular from acrylic acid, methacrylic acid, crotonic acid, itaconic acid and maleic acid. It is preferably acrylic or methacrylic acid.

The copolymer can comprise a monomer (b) comprising monoethylenic unsaturation which does not have surfactant property. The preferred monomers are those which give water-insoluble polymers when they are homopolymerized. They can be chosen, for example, from $C_1$-$C_4$ alkyl acrylates and methacrylates, such as methyl acrylate, ethyl acrylate, butyl acrylate or the corresponding methacrylates. The more particularly preferred monomers are methyl acrylate and ethyl acrylate. The other monomers which can be used are, for example, styrene, vinyltoluene, vinyl acetate, acrylonitrile and vinylidene chloride. Unreactive monomers are preferred, these monomers being those in which the single ethylenic group is the only group which is reactive under the polymerization conditions. However, monomers which comprise groups which react under the effect of heat, such as hydroxyethyl acrylate, can optionally be used.

The monomer (c) is obtained by reaction of an acrylic monomer comprising α,β-monoethylenic unsaturation, such as (a), or of an isocyanate monomer comprising monoethylenic unsaturation with a monohydric nonionic amphiphilic compound or a primary or secondary fatty amine.

The monohydric nonionic amphiphilic compounds or the primary or secondary fatty amines used to produce the nonionic monomer (c) are well known. The monohydric nonionic amphiphilic compounds are generally alkoxylated hydrophobic compounds comprising an alkylene oxide forming the hydrophilic part of the molecule. The hydrophobic compounds are generally composed of an aliphatic alcohol or an alkylphenol, in which compounds a carbonaceous chain comprising at least six carbon atoms constitutes the hydrophobic part of the amphiphilic compound.

The preferred monohydric nonionic amphiphilic compounds are compounds having the following formula (V):

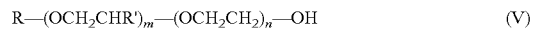

$$R—(OCH_2CHR')_m—(OCH_2CH_2)_n—OH \qquad (V)$$

in which R is chosen from alkyl or alkylene groups comprising from 6 to 30 carbon atoms and alkylaryl groups having alkyl radicals comprising from 8 to 30 carbon atoms, R' is chosen from alkyl groups comprising from 1 to 4 carbon atoms, n is a mean number ranging from approximately 1 to 150 and m is a mean number ranging from approximately 0 to 50, provided that n is at least as great as m.

Preferably, in the compounds of formula (V), the R group is chosen from alkyl groups comprising from 12 to 26 carbon atoms and alkylphenyl groups in which the alkyl group is $C_8$-$C_{13}$; the R' group is the methyl group; m=0 and n=1 to 25.

The preferred primary and secondary fatty amines are composed of one or two alkyl chains comprising from 6 to 30 carbon atoms.

The monomer used to form the nonionic urethane monomer (c) can be chosen from highly varied compounds. Use may be made of any compound comprising a copolymerizable unsaturation, such as an acrylic, methacrylic or allylic unsaturation. The monomer (c) can be obtained in particular from an isocyanate comprising monoethylenic unsaturation, such as, in particular, α,α-dimethyl-m-isopropenylbenzyl isocyanate.

The monomer (c) can be chosen in particular from acrylates, methacrylates or itaconates of oxyethylenated (1 to 50 EO) $C_6$-$C_{30}$ fatty alcohol, such as steareth-20 methacrylate, oxyethylenated (25 EO) behenyl methacrylate, oxyethylenated (20 EO) monocetyl itaconate, oxyethylenated (20 EO) monostearyl itaconate or the acrylate modified by polyoxyethylenated (25 EO) $C_{12}$-$C_{24}$ alcohols and from dimethyl-m-isopropenylbenzyl isocyanates of oxyethylenated (1 to 50 EO) $C_6$-$C_{30}$ fatty alcohol, such as, in particular, the dimethyl-m-isopropenylbenzyl isocyanate of oxyethylenated behenyl alcohol.

According to a specific embodiment of the present invention, the anionic polymer is chosen from acrylic terpolymers obtained from (a) a carboxylic acid comprising α,β-ethylenic unsaturation, (b) a non-surface-active monomer comprising ethylenic unsaturation other than (a), and (c) a nonionic urethane monomer which is the reaction product of a monohydric nonionic amphiphilic compound with an isocyanate comprising monoethylenic unsaturation.

Mention may in particular be made, as anionic polymers comprising at least one hydrophobic chain, of the acrylic acid/ethyl acrylate/alkyl acrylate terpolymer, such as the product as a 30% aqueous dispersion sold under the name Acusol 823 by Rohm & Haas; the acrylates/steareth-20 methacrylate copolymer, such as the product sold under the name Aculyn 22 by Rohm & Haas; the (meth)acrylic acid/ethyl acrylate/oxyethylenated (25 EO) behenyl methacrylate terpolymer, such as the product as an aqueous emulsion sold under the name Aculyn 28 by Rohm & Haas; the acrylic acid/oxyethylenated (20 EO) monocetyl itaconate copolymer, such as the product as a 30% aqueous dispersion sold under the name Structure 3001 by National Starch; the acrylic acid/oxyethylenated (20 EO) monostearyl itaconate copolymer, such as the product as a 30% aqueous dispersion sold under the name Structure 2001 by National Starch; the acrylates/acrylate modified by polyoxyethylenated (25 EO) $C_{12}$-$C_{24}$ alcohols copolymer, such as the 30-32% copolymer latex sold under the name Synthalen W2000 by 3V SA; or the methacrylic acid/methyl acrylate/dimethyl-meta-isopropenylbenzyl isocyanate of ethoxylated behenyl alcohol terpolymer, such as the product as a 24% aqueous dispersion and comprising 40 ethylene oxide groups disclosed in the document EP-A-0 173 109.

It may be preferable that the anionic polymer be selected from the group consisting of polysaccharides such as alginic acid, hyaluronic acid, and cellulose polymers (e.g., cellulose gum, hydroxyethylcellulose, hydroxypropylcellulose, methylcellulose, ethylhydroxyethylcellulose, and carboxymethylcellulose), anionic (co)polyamino acids such as (co)polyglutamic acids, (co)poly(meth)acrylic acids, (co)polyamic acids, (co)polystyrene sulfonate, (co)poly(vinyl sulfates), dextran sulfate, chondroitin sulfate, (co)polymaleic acids, (co)polyfumaric acids, maleic anhydride (co)polymers, and salts thereof.

The maleic anhydride copolymer may comprise one or more maleic anhydride comonomers, and one or more comonomers chosen from vinyl acetate, vinyl alcohol, vinylpyrrolidone, olefins comprising from 2 to 20 carbon atoms, and styrene.

Thus, the "maleic anhydride copolymer" is understood to mean any polymer obtained by copolymerization of one or more maleic anhydride comonomers and of one or more comonomers chosen from vinyl acetate, vinyl alcohol, vinylpyrrolidone, olefins comprising from 2 to 20 carbon atoms, such as octadecene, ethylene, isobutylene, diisobutylene or isooctylene, and styrene, the maleic anhydride comonomers optionally being partially or completely hydrolysed. Use will preferably be made of hydrophilic polymers, that is to say polymers having a solubility of water of greater than or equal to 2 g/l.

It may be preferable to use copolymers obtained by copolymerization of one or more maleic anhydride units of which the maleic anhydride units are in the hydrolysed form, and more preferably in the form of alkaline salts, for example in the form of ammonium, sodium, potassium or lithium salts.

In an advantageous aspect of the present invention, the maleic anhydride copolymer may have a molar fraction of maleic anhydride units of between 0.1 and 1, more preferably between 0.4 and 0.9.

The weight-average molar mass of the maleic anhydride copolymer may be between 1,000 and 500,000, and preferably between 1,000 and 50,000.

It is preferable that the maleic anhydride copolymer be a styrene/maleic anhydride copolymer, and more preferably sodium styrene/maleic anhydride copolymer.

Use will preferably be made of a copolymer of styrene and of maleic anhydride in a 50/50 ratio.

Use may be made, for example, of the styrene/maleic anhydride (50/50) copolymer, in the form of an ammonium salt at 30% in water, sold under the reference SMA1000H® by Cray Valley or the styrene/maleic anhydride (50/50) copolymer, in the form of a sodium salt at 40% in water, sold under the reference SMA1000HNa® by Cray Valley.

The amount of the anionic polymer(s) in the composition according to the present invention may be from 0.001% by weight or more, preferably 0.01% by weight or more, and more preferably from 0.1% by weight or more, relative to the total weight of the composition.

The amount of the anionic polymer(s) in the composition according to the present invention may be from 20% by weight or less, preferably from 15% by weight or less, and more preferably from 15% by weight or less, relative to the total weight of the composition.

The amount of the anionic polymer(s) in the composition according to the present invention may be from 0.001% to 20% by weight, preferably from 0.01% to 15% by weight, and more preferably from 0.1% to 15% by weight, relative to the total weight of the composition.

(Cosmetic Active Ingredient)

The composition according to the present invention may comprise at least one cosmetic active ingredient. There is no limitation to the cosmetic active ingredient. Two or more cosmetic active ingredients may be used in combination. Thus, a single type of cosmetic active ingredient or a combination of different types of cosmetic active ingredients may be used.

Among the cosmetic active ingredients to be used, mention may be made of UV filters, anti-oxidants, cleansing agents, free radical scavengers, moisturizers, whitening agents, liporegulators, anti-acne agents, antidandruff agents, anti-aging agents, softeners, anti-wrinkle agents, keratolitic agents, anti-inflammatory agents, fresheners, healing agents, vascular protectors, antibacterial agents, antifungal agents, antiperspirants, deodorants, skin conditioners, anesthetics, immunomodulators, nourishing agents, and sebum absorbers or moisture absorbers.

It is preferable that the (b) crosslinker be able to function as a cosmetic active agent. If the (b) crosslinker can function as a cosmetic active agent, it may not be necessary for the composition according to the present invention to include cosmetic active agent(s).

The composition according to the present invention may comprise the cosmetic active ingredient(s) in an amount of from 0.01% to 25% by weight, preferably from 0.1% to 20% by weight, more preferably from 1% to 15% by weight, and even more preferably from 2% to 10% by weight, relative to the total weight of the composition.

UV Filter

According to a preferred embodiment of the present invention, the cosmetic active ingredient may be selected from UV filters.

There is no limit to the type of UV filter. Two or more types of UV filters may be used in combination. Thus, a single type of UV filter or a combination of different types of UV filters may be used. The UV filter can be selected from the group consisting of an inorganic UV filter, an organic UV filter, and a mixture thereof.

Inorganic UV Filter

The composition according to the present invention may comprise at least one inorganic UV filter. If two or more inorganic UV filters are used, they may be the same or different, preferably the same.

The inorganic UV filter used for the present invention may be active in the UV-A and/or UV-B region. The inorganic UV filter may be hydrophilic and/or lipophilic. The inorganic UV filter is preferably insoluble in solvents such as water and ethanol commonly used in cosmetics.

It is preferable that the inorganic UV filter be in the form of a fine particle such that the mean (primary) particle diameter thereof ranges from 1 nm to 50 nm, preferably 5 nm to 40 nm, and more preferably 10 nm to 30 nm. The mean (primary) particle size or mean (primary) particle diameter here is an arithmetic mean diameter.

The inorganic UV filter can be selected from the group consisting of silicon carbide, metal oxides which may or may not be coated, and mixtures thereof.

Preferably, the inorganic UV filters may be selected from pigments (mean size of the primary particles: generally from 5 nm to 50 nm, preferably from 10 nm to 50 nm) formed of metal oxides, such as, for example, pigments formed of titanium oxide (amorphous or crystalline in the rutile and/or anatase form), iron oxide, zinc oxide, zirconium oxide or cerium oxide, which are all UV photoprotective agents that are well known per se. Preferably, the inorganic UV filters may be selected from titanium oxide, zinc oxide, and more preferably titanium oxide.

The inorganic UV filter may or may not be coated. The inorganic UV filter may have at least one coating. The coating may comprise at least one compound selected from the group consisting of alumina, silica, aluminum hydroxide, silicones, silanes, fatty acids or salts thereof (such as sodium, potassium, zinc, iron, or aluminum salts), fatty alcohols, lecithin, amino acids, polysaccharides, proteins, alkanolamines, waxes such as beeswax, (meth)acrylic polymers, organic UV filters, and (per)fluoro compounds.

It is preferable for the coating to include at least one organic UV filter. As the organic UV filter in the coating, a dibenzoylmethane derivative such as butyl methoxydibenzoylmethane (Avobenzone) and 2,2'-Methylenebis[6-(2H-Benzotriazol-2-yl)-4-(1,1,3,3-Tetramethyl-Butyl)Phenol] (Methylene Bis-Benzotriazolyl Tetramethylbutylphenol) marketed as "TINOSORB M" by BASF may be preferable.

In a known manner, the silicones in the coating(s) may be organosilicon polymers or oligomers comprising a linear or cyclic and branched or cross-linked structure, of variable molecular weight, obtained by polymerization and/or polycondensation of suitable functional silanes and essentially composed of repeated main units in which the silicon atoms are connected to one another via oxygen atoms (siloxane bond), optionally substituted hydrocarbon radicals being connected directly to said silicon atoms via a carbon atom.

The term "silicones" also encompasses silanes necessary for their preparation, in particular alkylsilanes.

The silicones used for the coating(s) can preferably be selected from the group consisting of alkylsilanes, polydialkylsiloxanes, and polyalkylhydrosiloxanes. More preferably still, the silicones are selected from the group consisting of octyltrimethylsilanes, polydimethylsiloxanes, and polymethylhydrosiloxanes.

Of course, the inorganic UV filters made of metal oxides may, before their treatment with silicones, have been treated with other surfacing agents, in particular, with cerium oxide, alumina, silica, aluminum compounds, silicon compounds, or their mixtures.

The coated inorganic UV filter may have been prepared by subjecting the inorganic UV filter to one or more surface treatments of a chemical, electronic, mechanochemical, and/or mechanical nature with any of the compounds as described above, as well as polyethylenes, metal alkoxides (titanium or aluminum alkoxides), metal oxides, sodium hexametaphosphate, and those shown, for example, in Cosmetics & Toiletries, February 1990, Vol. 105, pp. 53-64.

The coated inorganic UV filters may be titanium oxides coated with:
  silica, such as the product "Sunveil" from Ikeda;
  silica and iron oxide, such as the product "Sunveil F" from Ikeda;
  silica and alumina, such as the products "Microtitanium Dioxide MT 500 SA" from Tayca, "Tioveil" from Tioxide, and "Mirasun TiW 60" from Rhodia;
  alumina, such as the products "Tipaque TTO-55 (B)" and "Tipaque TTO-55 (A)" from Ishihara, and "UVT 14/4" from Kemira;
  alumina and aluminum stearate, such as the product "Microtitanium Dioxide MT 100 T, MT 100 TX, MT 100 Z or MT-01" from Tayca, the products "Solaveil CT-10 W" and "Solaveil CT 100" from Uniqema, and the product "Eusolex T-AVO" from Merck;
  alumina and aluminum laurate, such as the product "Microtitanium Dioxide MT 100 S" from Tayca;
  iron oxide and iron stearate, such as the product "Microtitanium Dioxide MT 100 F" from Tayca;
  zinc oxide and zinc stearate, such as the product "BR351" from Tayca;
  silica and alumina and treated with a silicone, such as the products "Microtitanium Dioxide MT 600 SAS", "Microtitanium Dioxide MT 500 SAS", and "Microtitanium Dioxide MT 100 SAS" from Tayca;
  silica, alumina, and aluminum stearate and treated with a silicone, such as the product "STT-30-DS" from Titan Kogyo;
  silica and treated with a silicone, such as the product "UV-Titan X 195" from Kemira;
  alumina and treated with a silicone, such as the products "Tipaque TTO-55 (S)" from Ishihara or "UV Titan M 262" from Kemira;
  triethanolamine, such as the product "STT-65-S" from Titan Kogyo;
  stearic acid, such as the product "Tipaque TTO-55 (C)" from Ishihara; or sodium hexametaphosphate, such as the product "Microtitanium Dioxide MT 150 W" from Tayca.

Other titanium oxide pigments treated with a silicone are preferably $TiO_2$ treated with octyltrimethylsilane and for which the mean size of the individual particles is from 25 and 40 nm, such as that marketed under the trademark "T 805" by Degussa Silices, $TiO_2$ treated with a polydimethylsiloxane and for which the mean size of the individual particles is 21 nm, such as that marketed under the trademark "70250 Cardre UF $TiO_2Si_3$" by Cardre, and anatase/rutile $TiO_2$ treated with a polydimethylhydrosiloxane and for which the mean size of the individual particles is 25 nm, such as that marketed under the trademark "Microtitanium Dioxide USP Grade Hydrophobic" by Color Techniques.

Preferably, the following coated $TiO_2$ can be used as the coated inorganic UV filter:
  Stearic acid (and) Aluminum Hydroxide (and) $TiO_2$, such as the product "MT-100 TV" from Tayca, with a mean primary particle diameter of 15 nm;
  Dimethicone (and) Stearic Acid (and) Aluminum Hydroxide (and) $TiO_2$, such as the product "SA-TTO-S4" from Miyoshi Kasei, with a mean primary particle diameter of 15 nm;
  Silica (and) $TiO_2$, such as the product "MT-100 WP" from Tayca, with a mean primary particle diameter of 15 nm;
  Dimethicone (and) Silica (and) Aluminum Hydroxide (and) $TiO_2$, such as the product "MT-Y02" and "MT-Y-110 M3S" from Tayca, with a mean primary particle diameter of 10 nm;
  Dimethicone (and) Aluminum Hydroxide (and) $TiO_2$, such as the product "SA-TTO-S3" from Miyoshi Kasei, with a mean primary particle diameter of 15 nm;

Dimethicone (and) Alumina (and) TiO$_2$, such as the product "UV TITAN M170" from Sachtleben, with a mean primary particle diameter of 15 nm; and Silica (and) Aluminum Hydroxide (and) Alginic Acid (and) TiO$_2$, such as the product "MT-100 AQ" from Tayca, with a mean primary particle diameter of 15 nm.

In terms of UV filtering ability, TiO$_2$ coated with at least one organic UV filter is more preferable. For example, Avobenzone (and) Stearic Acid (and) Aluminum Hydroxide (and) TiO$_2$, such as the product "HXMT-100ZA" from Tayca, with a mean primary particle diameter of 15 nm, can be used.

The uncoated titanium oxide pigments are, for example, marketed by Tayca under the trademarks "Microtitanium Dioxide MT500B" or "Microtitanium Dioxide MT600B", by Degussa under the trademark "P 25", by Wacker under the trademark "Oxyde de titane transparent PW", by Miyoshi Kasei under the trademark "UFTR", by Tomen under the trademark "ITS", and by Tioxide under the trademark "Tioveil AQ".

The uncoated zinc oxide pigments are, for example:

those marketed under the trademark "Z-cote" by Sunsmart;

those marketed under the trademark "Nanox" by Elementis; and those marketed under the trademark "Nanogard WCD 2025" by Nanophase Technologies.

The coated zinc oxide pigments are, for example:

those marketed under the trademark "Oxide Zinc CS-5" by Toshiba (ZnO coated with polymethylhydrosiloxane);

those marketed under the trademark "Nanogard Zinc Oxide FN" by Nanophase Technologies (as a 40% dispersion in Finsolv TN, C$_{12}$-C$_{15}$ alkyl benzoate);

those marketed under the trademark "Daitopersion Zn-30" and "Daitopersion Zn-50" by Daito (dispersions in oxyethylenated polydimethylsiloxane/cyclopolymethylsiloxane comprising 30% or 50% of zinc nano-oxides coated with silica and polymethylhydrosiloxane);

those marketed under the trademark "NFD Ultrafine ZnO" by Daikin (ZnO coated with phosphate of perfluoroalkyl and a copolymer based on perfluoroalkylethyl as a dispersion in cyclopentasiloxane);

those marketed under the trademark "SPD-Z1" by Shin-Etsu (ZnO coated with a silicone-grafted acrylic polymer dispersed in cyclodimethylsiloxane);

those marketed under the trademark "Escalol Z100" by ISP (alumina-treated ZnO dispersed in an ethylhexyl methoxycinnamate/PVP-hexadecene copolymer/methicone mixture);

those marketed under the trademark "Fuji ZnO-SMS-10" by Fuji Pigment (ZnO coated with silica and polymethylsilsesquioxane); and those marketed under the trademark "Nanox Gel TN" by Elementis (ZnO dispersed at 55% in C$_{12}$-C$_{15}$ alkyl benzoate with hydroxystearic acid polycondensate).

The uncoated cerium oxide pigments are marketed, for example, under the trademark "Colloidal Cerium Oxide" by Rhone-Poulenc.

The uncoated iron oxide pigments are, for example, marketed by Arnaud under the trademarks "Nanogard WCD 2002 (FE 45B)", "Nanogard Iron FE 45 BL AQ", "Nanogard FE 45R AQ", and "Nanogard WCD 2006 (FE 45R)", or by Mitsubishi under the trademark "TY-220".

The coated iron oxide pigments are, for example, marketed by Arnaud under the trademarks "Nanogard WCD 2008 (FE 45B FN)", "Nanogard WCD 2009 (FE 45B 556)", "Nanogard FE 45 BL 345", and "Nanogard FE 45 BL", or by BASF under the trademark "Oxyde de fer transparent".

Mention may also be made of mixtures of metal oxides, in particular, of titanium dioxide and of cerium dioxide, including a mixture of equal weights of titanium dioxide coated with silica and of cerium dioxide coated with silica marketed by Ikeda under the trademark "Sunveil A", and also a mixture of titanium dioxide and of zinc dioxide coated with alumina, with silica and with silicone, such as the product "M 261" marketed by Kemira, or coated with alumina, with silica, and with glycerol, such as the product "M 211" marketed by Kemira.

Coated inorganic UV filters are preferable, because the UV filtering effects of the inorganic UV filters can be enhanced. In addition, the coating(s) may help uniformly or homogeneously disperse the UV filters in the composition according to the present invention.

Organic UV Filter

The composition according to the present invention may comprise at least one organic UV filter. If two or more organic UV filters are used, they may be the same or different, preferably the same.

The organic UV filter used for the present invention may be active in the UV-A and/or UV-B region. The organic UV filter may be hydrophilic and/or lipophilic.

The organic UV filter may be solid or liquid. The terms "solid" and "liquid" mean solid and liquid, respectively, at 25° C. under 1 atm.

The organic UV filter can be selected from the group consisting of anthranilic compounds; dibenzoylmethane compounds; cinnamic compounds; salicylic compounds; camphor compounds; benzophenone compounds; β,β-diphenylacrylate compounds; triazine compounds; benzotriazole compounds; benzalmalonate compounds; benzimidazole compounds; imidazoline compounds; bis-benzoazolyl compounds; p-aminobenzoic acid (PABA) compounds; methylenebis(hydroxyphenylbenzotriazole) compounds; benzoxazole compounds; screening polymers and screening silicones; dimers derived from α-alkylstyrene; 4,4-diarylbutadiene compounds; guaiazulene and derivatives thereof; rutin and derivatives thereof; and mixtures thereof.

Mention may be made, as examples of the organic UV filter(s), of those denoted below under their INCI names, and mixtures thereof.

Anthranilic compounds: Menthyl anthranilate, marketed under the trademark "Neo Heliopan MA" by Haarmann and Reimer.

Dibenzoylmethane compounds: Butyl methoxydibenzoylmethane, marketed in particular under the trademark "Parsol 1789" by Hoffmann-La Roche; and isopropyl dibenzoylmethane.

Cinnamic compounds: Ethylhexyl methoxycinnamate, marketed in particular under the trademark "Parsol MCX" by Hoffmann-La Roche; isopropyl methoxycinnamate; isopropoxy methoxycinnamate; isoamyl methoxycinnamate, marketed under the trademark "Neo Heliopan E 1000" by Haarmann and Reimer; cinoxate (2-ethoxyethyl-4-methoxy cinnamate); DEA methoxycinnamate; diisopropyl methylcinnamate; and glyceryl ethylhexanoate dimethoxycinnamate.

Salicylic compounds: Homosalate (homomentyl salicylate), marketed under the trademark "Eusolex HMS" by Rona/EM Industries; ethylhexyl salicylate, marketed under the trademark "Neo Heliopan OS" by Haarmann and Reimer; glycol salicylate; butyloctyl salicylate; phenyl salicylate; dipropyleneglycol salicylate, marketed under the trademark "Dipsal" by Scher; and TEA salicylate, marketed under the trademark "Neo Heliopan TS" by Haarmann and Reimer.

Camphor compounds, in particular, benzylidenecamphor derivatives: 3-benzylidene camphor, manufactured under the trademark "Mexoryl SD" by Chimex; 4-methylbenzylidene camphor, marketed under the trademark "Eusolex 6300" by Merck; benzylidene camphor sulfonic acid, manufactured under the trademark "Mexoryl SL" by Chimex; camphor benzalkonium methosulfate, manufactured under the trademark "Mexoryl SO" by Chimex; terephthalylidene dicamphor sulfonic acid, manufactured under the trademark "Mexoryl SX" by Chimex; and polyacrylamidomethyl benzylidene camphor, manufactured under the trademark "Mexoryl SW" by Chimex.

Benzophenone compounds: Benzophenone-1 (2,4-dihydroxybenzophenone), marketed under the trademark "Uvinul 400" by BASF; benzophenone-2 (Tetrahydroxybenzophenone), marketed under the trademark "Uvinul D50" by BASF; Benzophenone-3 (2-hydroxy-4-methoxybenzophenone) or oxybenzone, marketed under the trademark "Uvinul M40" by BASF; benzophenone-4 (hydroxymethoxy benzophonene sulfonic acid), marketed under the trademark "Uvinul MS40" by BASF; benzophenone-5 (Sodium hydroxymethoxy benzophenone Sulfonate); benzophenone-6 (dihydroxy dimethoxy benzophenone); marketed under the trademark "Helisorb 11" by Norquay; benzophenone-8, marketed under the trademark "Spectra-Sorb UV-24" by American Cyanamid; benzophenone-9 (Disodium dihydroxy dimethoxy benzophenonedisulfonate), marketed under the trademark "Uvinul DS-49" by BASF; benzophenone-12, and n-hexyl 2-(4-diethylamino-2-hydroxybenzoyl)benzoate (UVINUL A+by BASF).

β,β-Diphenylacrylate compounds: Octocrylene, marketed in particular under the trademark "Uvinul N539" by BASF; and Etocrylene, marketed in particular under the trademark "Uvinul N35" by BASF.

Triazine compounds: Diethylhexyl butamido triazone, marketed under the trademark "Uvasorb HEB" by Sigma 3V; 2,4,6-tris(dineopentyl 4'-aminobenzalmalonate)-s-triazine, bis-ethylhexyloxyphenol methoxyphenyl triazine marketed under the trademark «TINOSORB S» by CIBA GEIGY, and ethylhexyl triazone marketed under the trademark «UVINUL T150» by BASF.

Benzotriazole compounds, in particular, phenylbenzotriazole derivatives: 2-(2H-benzotriazole-2-yl)-6-dodecyl-4-methylpheno, branched and linear; and those described in U.S. Pat. No. 5,240,975.

Benzalmalonate compounds: Dineopentyl 4'-methoxybenzalmalonate, and polyorganosiloxane comprising benzalmalonate functional groups, such as polysilicone-15, marketed under the trademark "Parsol SLX" by Hoffmann-LaRoche.

Benzimidazole compounds, in particular, phenylbenzimidazole derivatives: Phenylbenzimidazole sulfonic acid, marketed in particular under the trademark "Eusolex 232" by Merck, and disodium phenyl dibenzimidazole tetrasulfonate, marketed under the trademark "Neo Heliopan AP" by Haarmann and Reimer.

Imidazoline compounds: Ethylhexyl dimethoxybenzylidene dioxoimidazoline propionate.

Bis-benzoazolyl compounds: The derivatives as described in EP-669,323 and U.S. Pat. No. 2,463,264.

Para-aminobenzoic acid compounds: PABA (p-aminobenzoic acid), ethyl PABA, Ethyl dihydroxypropyl PABA, pentyl dimethyl PABA, ethylhexyl dimethyl PABA, marketed in particular under the trademark "Escalol 507" by ISP, glyceryl PABA, and PEG-25 PABA, marketed under the trademark "Uvinul P25" by BASF.

Methylene bis-(hydroxyphenylbenzotriazol) compounds, such as 2,2'-methylenebis[6-(2H-benzotriazol-2-yl)-4-methyl-phenol] marketed in the solid form under the trademark "Mixxim BB/200" by Fairmount Chemical, 2,2'-methylenebis[6-(2H-benzotriazol-2-yl)-4-(1,1,3,3-tetramethylbutyl)phenol] marketed in the micronized form in aqueous dispersion under the trademark "Tinosorb M" by BASF, or under the trademark "Mixxim BB/100" by Fairmount Chemical, and the derivatives as described in U.S. Pat. Nos. 5,237,071 and 5,166,355, GB-2,303,549, DE-197,26,184 and EP-893,119, and Drometrizole trisiloxane, marketed under the trademark "Silatrizole" by Rhodia Chimie or "Mexoryl XL" by Chimex, as represented below.

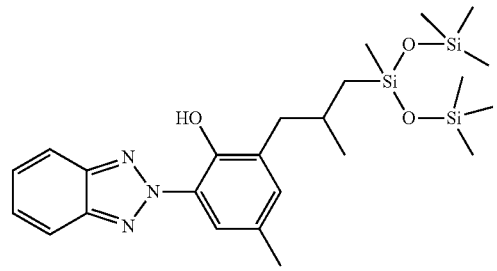 [SMILES: Cc1cc(CC(C)C[Si](C)(O[Si](C)(C)C)O[Si](C)(C)C)c(O)c(-n2nc3ccccc3n2)c1]

Benzoxazole compounds: 2,4-bis[5-1(dimethylpropyl) benzoxazol-2-yl-(4-phenyl)imino]-6-(2-ethylhexyl) imino-1,3,5-triazine, marketed under the trademark Uvasorb K2A by Sigma 3V.

Screening polymers and screening silicones: The silicones described in WO 93/04665.

Dimers derived from α-alkylstyrene: The dimers described in DE-19855649.

4,4-Diarylbutadiene compounds: 1,1-dicarboxy(2,2'-dimethylpropyl)-4,4-diphenylbutadiene.

It is preferable that the organic UV filter(s) be selected from the group consisting of: butyl methoxydibenzoylmethane, ethylhexyl methoxycinnamate, homosalate, ethylhexyl salicylate, octocrylene, phenylbenzimidazole sulfonic acid, benzophenone-3, benzophenone-4, benzophenone-5, n-hexyl 2-(4-diethylamino-2-hydroxybenzoyl)benzoate, 1,1'-(1,4-piperazinediyl)bis[1-[2-[4-(diethylamino)-2-hydroxybenzoyl]phenyl]-methanone 4-methylbenzylidene camphor, terephthalylidene dicamphor sulfonic acid, disodium phenyl dibenzimidazole tetrasulfonate, ethylhexyl triazone, bis-ethylhexyloxyphenol methoxyphenyl triazine, diethylhexyl butamido triazone, 2,4,6-tris(dineopentyl 4'-aminobenzalmalonate)-s-triazine, 2,4,6-tris(diisobutyl 4'-aminobenzalmalonate)-s-triazine, 2,4-bis-(n-butyl 4'-aminobenzalmalonate)-6-[(3-{1,3,3,3-tetramethyl-1-[(trimethylsilyloxy]-disiloxanyl}propyl)amino]-s-triazine, 2,4,6-tris-(di-phenyl)-triazine, 2,4,6-tris-(ter-phenyl)-triazine, methylene bis-benzotriazolyl tetramethylbutylphenol, drometrizole trisiloxane, polysilicone-15, dineopentyl 4'-methoxybenzalmalonate, 1,1-dicarboxy(2,2'-dimethylpropyl)-4,4-diphenylbutadiene, 2,4-bis[5-1 (dimethylpropyl)benzoxazol-2-yl-(4-phenyl)imino]-6-(2-ethylhexyl) imino-1,3,5-triazine, camphor benzylkonium methosulfate and mixtures thereof.
(pH)

The pH of the composition according to the present invention may be from 3 to 9, preferably from 3.5 to 8, and more preferably from 4 to 7.

The pH of the composition may be adjusted by adding at least one alkaline agent and/or at least one acid. The pH of the composition may also be adjusted by adding at least one buffering agent.
(Alkaline Agent)

The composition according to the present invention may comprise at least one alkaline agent. Two or more alkaline agents may be used in combination. Thus, a single type of alkaline agent or a combination of different types of alkaline agents may be used.

The alkaline agent may be an inorganic alkaline agent. It is preferable that the inorganic alkaline agent be selected from the group consisting of ammonia; alkaline metal hydroxides; alkaline earth metal hydroxides; alkaline metal phosphates and monohydrogenophosphates such as sodium phosphate or sodium monohydrogeno phosphate.

As examples of the inorganic alkaline metal hydroxides, mention may be made of sodium hydroxide and potassium hydroxide. As examples of the alkaline earth metal hydroxides, mention may be made of calcium hydroxide and magnesium hydroxide. As inorganic alkaline agent, sodium hydroxide is preferable.

The alkaline agent may be an organic alkaline agent. It is preferable that the organic alkaline agent be selected from the group consisting of monoamines and derivatives thereof; diamines and derivatives thereof; polyamines and derivatives thereof; basic amino acids and derivatives thereof; oligomers of basic amino acids and derivatives thereof; polymers of basic amino acids and derivatives thereof; urea and derivatives thereof; and guanidine and derivatives thereof.

As examples of the organic alkaline agents, mention may be made of alkanolamines such as mono-, di- and tri-ethanolamine, and isopropanolamine; urea, guanidine and their derivatives; basic amino acids such as lysine, ornithine or arginine; and diamines such as those described in the structure below:

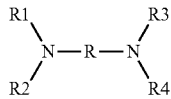

wherein R denotes an alkylene such as propylene optionally substituted by a hydroxyl or a $C_1$-$C_4$ alkyl radical, and $R_1$, $R_2$, $R_3$ and $R_4$ independently denote a hydrogen atom, an alkyl radical or a $C_1$-$C_4$ hydroxyalkyl radical, which may be exemplified by 1,3-propanediamine and derivatives thereof. Arginine, urea and monoethanolamine are preferable.

The alkaline agent(s) may be used in a total amount of from 0.001% to 10% by weight, preferably from 0.01% to 5% by weight, more preferably from 0.1% to 1% by weight, relative to the total weight of the composition, depending on their solubility.
(Acid)

The composition according to the present invention may comprise at least one acid. Two or more acids may be used in combination. Thus, a single type of acid or a combination of different types of acids may be used.

As the acid, mention may be made of any inorganic or organic acids which are commonly used in cosmetic products. A monovalent acid and/or a polyvalent acid may be used. A monovalent acid such as citric acid, lactic acid, sulfuric acid, phosphoric acid and hydrochloric acid (HCl) may be used. HCl is preferable.

The acid(s) may be used in a total amount of from 0.001% to 10% by weight, preferably from 0.01% to 5% by weight, more preferably from 0.1% to 1% by weight, relative to the total weight of the composition, depending on their solubility.
(Buffering Agent)

The composition according to the present invention may comprise at least one buffering agent. Two or more buffering agents may be used in combination. Thus, a single type of buffering agent or a combination of different types of buffering agents may be used.

As the buffering agent, mention may be made of an acetate buffer (for example, acetic acid+sodium acetate), a phosphate buffer (for example, sodium dihydrogen phosphate+di-sodium hydrogen phosphate), a citrate buffer (for example, citric acid+sodium citrate), a borate buffer (for example, boric acid+sodium borate), a tartrate buffer (for example, tartaric acid+sodium tartrate dihydrate), Tris buffer (for example, tris(hydroxymethyl)aminomethane), and Hepes buffer (4-(2-hydroxyethyl)-1-piperazineethanesulfonic acid).
(Optional Additives)

The composition according to the present invention may comprise, in addition to the aforementioned components, components typically employed in cosmetics, specifically, such as dyes, powders, thickeners, organic non-volatile solvents, silicones and silicone derivatives, natural extracts derived from animals or vegetables, waxes, and the like, within a range which does not impair the effects of the present invention.

The composition according to the present invention may comprise the above optional additive(s) in an amount of from 0.001% to 10% by weight, preferably from 0.01% to 5% by weight, and more preferably from 0.1% to 1% by weight, relative to the total weight of the composition.
[Composition]

The composition according to the present invention may be intended to be used as a cosmetic composition. Thus, the cosmetic composition according to the present invention may be intended for application onto a keratin substance. Keratin substance here means a material containing keratin as a main constituent element, and examples thereof include the skin, scalp, nails, lips, hair, and the like. Thus, it is preferable that the cosmetic composition according to the present invention be used for a cosmetic process for the keratin substance, in particular skin.

Thus, the cosmetic composition according to the present invention may be a skin cosmetic composition, preferably a skin care composition or a skin makeup composition, in particular a composition for protecting skin from UV light and/or pollutants in the air.

The composition according to the present invention may be in any form such as a dispersion, an emulsion, a gel, and a paste. The composition according to the present invention may be in the form of an emulsion such as W/O, O/W, W/O/W and O/W/O, preferably, an O/W emulsion.

In one embodiment, the composition according to the present invention further comprises at least one gas, and is in the form of a foam.

The type of gas is not limited. Thus, a single type of gas may be used. For example, oxygen, nitrogen, carbon dioxide, hydrocarbon gas such as those derived from LPG, and dimethylether gas may be used. On the other hand, a mixture of gases may be used for the gas. Thus, a mixture of oxygen, nitrogen and carbon dioxide may be used. It may be preferable that air be used as the gas. Thus, it may be preferable that the gas comprise or consist of air.

The composition according to the present invention can be prepared by mixing the above essential and optional ingredients in accordance with any of the processes which are well known to those skilled in the art.

It is preferable that the (a) at least one cationic polysaccharide, (b) at least one crosslinker having three or more acid groups or salt thereof, and (d) at least one physiologically acceptable volatile medium be mixed to prepare a DIC gel solution, and then, the DIC gel solution be mixed with (c) at least one oil.

The composition according to the present invention may include at least one surfactant. However, it is preferable that the amount of the surfactant(s) in the composition according to the present invention be limited.

The composition according to the present invention may optionally comprise at least one surfactant in an amount of 1% by weight or less, preferably 0.5% by weight or less, and more preferably 0.3% by weight or less, relative to the total weight of the composition.

It is preferable that the composition according to the present invention be substantially free from surfactant. The term "substantially free from surfactant" means that the composition according to the present invention comprises no surfactant, or comprises at least one surfactant in an amount of 4% by weight or less, preferably 2% by weight or less, and more preferably 1% by weight or less, relative to the total weight of the composition.

The surfactant may be selected from the group consisting of anionic surfactants, amphoteric surfactants, cationic surfactants, and nonionic surfactants. Two or more surfactants may be used in combination. Thus, a single type of surfactant or a combination of different types of surfactants may be used.

[Cosmetic Process and Use]

The present invention also relates to a cosmetic process for a keratin substrate such as skin, comprising the steps of foaming the composition according to the present invention and applying the foam to the keratin substrate.

The cosmetic process here means non-therapeutic cosmetic method for caring for and/or making up the surface of a keratin substrate such as skin.

The present invention also relates to a use of (a) at least one cationic polysaccharide, and (b) at least one crosslinker having three or more acid groups or salt thereof in (d) at least one physiologically acceptable medium in a composition in order to prepare a stable foam wherein the composition comprises (c) at least one oil in an amount of 10% by weight or more, preferably 15% by weight or more, and more preferably 20% by weight or more, relative to the total weight of the composition.

The above explanations regarding the ingredients (a) to (d) for the composition according to the present invention can apply to those in the above use.

[Foaming Product]

The present invention also relates to a foaming product comprising:

at least one container comprising the composition according to the present invention; and
at least one dispenser, wherein
the dispenser is capable of discharging the composition in the form of a foam.

The compositions according to the present invention can be packaged in a container for example in a jar, in a tube, in a pump-dispenser bottle, in a foamer or in an aerosol device that is customary in the cosmetics industry.

The material of the container may be any conventional material such as metals and resins. It may be preferable that the material is selected such that the container is pressure-resistant.

The structure of the dispenser is not limited as long as it is capable of discharging the composition according to the present invention in the form of a foam.

The dispenser may comprise at least one nozzle and at least one valve which can control the flow of the composition according to the present invention from the container to the nozzle. The valve can be opened by, for example, pushing a button and the like which will open the valve. It is preferable that the valve be closed in a normal position, and can be in an open position when the dispenser is activated by, for example, pushing a button and the like which is linked to the valve.

The compositions according to the present invention can, when they are intended to be packaged in an aerosol device, contain one or more propellant gases. As the propellant, any conventional one can be used. As the propellant, mention may be made of liquefied gas such as LPG and dimethylether, compressed gas such as nitrogen gas and carbon dioxide gas, and mixtures thereof. In this embodiment, the foam prepared by the foaming product according to the present invention comprises bubbles of gas derived from the propellant.

The amount of the liquefied gas may be 0.5-20% by weight, preferably 1-15% by weight, and more preferably 2-12% by weight, relative to the total weight of the composition according to the present invention and the liquefied gas.

In another embodiment, the foaming product according to the present invention may further comprise either a squeezable wall or a pump for transferring the composition from the container into the dispenser. The pump is connected to the container and the dispenser, wherein the pump is capable of mixing the composition according to the present invention with at least one gas to prepare a foam and of conveying the foam to the dispenser. The foam can be formed by forcing the composition to pass through a material comprising a porous substance such as a sintered material, a filtering grid made of plastic or of metal, or similar structures. There is no limitation for the type of the pump. For example, a mechanical pump which can be manually operated may be used. In this embodiment, no propellant is necessary. It is preferable that air be used as the gas.

EXAMPLES

The present invention will be described in a more detailed manner by way of examples. However, they should not be construed as limiting the scope of the present invention.

Example 1

(Preparation)

A foaming composition according to Example 1 was prepared by mixing the ingredients shown in Table 1. The numerical values for the amounts of the ingredients shown in Table 1 are all based on "% by weight" as active raw materials.

TABLE 1

| Example 1 | |
| --- | --- |
| Polyquaternium-67 | 0.53 |
| Phytic Acid | 0.20 |
| Water | 69.27 |
| Dimethicone | 30.00 |

First, 0.53 g of polyquaternium-67 (PQ-67) as a polycation and 69.27 g of water were charged into a beaker. They were heated to 70° C. and mixed with a stirrer for 1 hour to prepare a solution. Next, 0.20 g of phytic acid was added to the solution to prepare a DIC-gel aqueous solution.

30 g of dimethicone (oil) was then added to the DIC-gel aqueous solution, and was mixed with a homogenizer at 6000 rpm for 20 minutes to obtain a foaming composition.

(Evaluation)

45 g of the foaming composition according to Example 1 and 5 g of LPG (0.31 MPa) as a propellant were charged into an aerosol bottle equipped with a dispenser. After shaking the aerosol bottle well, the dispenser was activated to discharge the foaming composition as a foam.

The foam was stable for more than 20 minutes.

Example 2-4 and Comparative Examples 1-2

(Preparations)

Foaming compositions according to Examples 2-4 and Comparative Examples 1-2 were prepared by mixing the components shown in Table 2. The numerical values for the amounts of the components shown in Table 2 are all based on "% by weight" as active raw materials.

TABLE 2

| | Ex. 2 | Ex. 3 | Ex. 4 | Comp. Ex. 1 | Comp. Ex. 2 |
| --- | --- | --- | --- | --- | --- |
| Water | qsp 100 | qsp 100 | qsp 100 | qsp 100 | qsp 100 |
| Polyquaternium-67 | 0.74 | 0.74 | 0.74 | — | — |
| Sodium Hydroxide | 0.09 | 0.09 | 0.09 | — | — |
| Phenoxyethanol | 0.5 | 0.5 | 0.5 | 0.5 | 0.5 |
| Laureth-4 | — | — | — | 1.13 | — |
| Polyglyceryl-2 Myristate | — | — | — | — | 1.13 |
| Phytic Acid | 0.15 | 0.15 | — | — | — |
| Citric Acid | — | — | 0.3 | — | — |
| Cyclopentasiloxane (and) Dimethiconol | 30 | 10 | 10 | 10 | 10 |
| Stability of Foam | Stable | Stable | Stable | Unstable | Unstable |

(Evaluations)

45 g of each of the foaming compositions according to Examples 2-4 and Comparative Examples 1-2 and 5 g of LPG (0.31 MPa) as propellant were charged into an aerosol bottle equipped with a dispenser. After shaking the aerosol bottle well, the dispenser was activated to discharge the foaming composition as a foam. The stability of the foam was visually observed and evaluated in accordance with the following criteria.

Stable: The foam was maintained for more than 1 minute
Unstable: The foam was broken within 1 minute The results of the evaluation are shown in Table 2.

It was found that DIC gels were able to stabilize a foam including a substantial amount of oil (cf. Examples 2 to 4), while conventional surfactants could not stabilize a foam including a substantial amount of oil (cf. Comparative Examples 1 and 2).

Example 5

(Preparation)

A foaming composition according to Example 5 was prepared by mixing the components shown in Table 3. The numerical values for the amounts of the components shown in Table 3 are all based on "% by weight" as active raw materials.

TABLE 3

| Example 5 | |
| --- | --- |
| Water | qsp 100 |
| Polyquaternium-67 | 0.37 |
| Polyquaternium-6 | 0.88 |
| Sodium Hydroxide | 0.09 |
| Cellulose Gum | 0.11 |
| Phenoxyethanol | 0.50 |
| Phytic Acid | 0.15 |
| Cyclopentasiloxane (and) Dimethiconol | 30.00 |

(Evaluation)

45 g of the foaming composition according to Example 5 and 5 g of LPG (0.31 MPa) as propellant were charged into an aerosol bottle equipped with a dispenser. After shaking the aerosol bottle well, the dispenser was activated to discharge the foaming composition as a foam.

A sensorial test for the foam was performed as follows.

The smoothness of a hair swatch was evaluated for 5 panelists in accordance with the criteria shown below and averaged. The result is shown in the cell of "Non-Treated Hair" and "Before Washing by Shampoo" in Table 4.

The foam thus obtained by the foaming composition according to Example 5 was applied onto the above untreated hair swatch. The smoothness of the treated hair swatch was evaluated for the same 5 panelists in accordance with the criteria shown below and averaged. The result is shown in the cell of "Example 5" and "Before Washing with Shampoo" in Table 4.

A conventional hair treatment product (L'Oreal Elseve Damage Care) was applied onto the above untreated hair swatch. The smoothness of the treated hair swatch was evaluated for the same 5 panelists in accordance with the criteria shown below and averaged. The result is shown in the cell of "Control" and "Before Washing with Shampoo" in Table 4.

Criteria
5: Very Good
4: Good
3: Fair
2: Poor
1: Very Poor

Next, the above untreated hair swatch was shampooed, and the smoothness of the washed hair swatch was then re-evaluated in the same manner. The result is shown in the cell of "Non-Treated Hair" and "After Washing by Shampoo" in Table 4.

The hair swatch treated with the foam obtained by the foaming composition according to Example 5 was shampooed, and the smoothness of the washed hair swatch was then re-evaluated in the same manner. The result is shown in the cell of "Example 5" and "After Washing with Shampoo" in Table 4.

The hair swatch treated with the conventional hair treatment product (L'Oreal Elseve Damage Care) was shampooed, and then, the smoothness of the washed hair was re-evaluated in the same manner. The result is shown in the cell of "Control" and "After Washing by Shampoo" in Table 4.

TABLE 4

|  | Before Washing with Shampoo | After Washing with Shampoo |
|---|---|---|
| Non-Treated Hair | 1 | 1 |
| Example 5 | 5 | 5 |
| Control | 5 | 3 |

Table 4 shows that the foam according to the present invention can provide cosmetic effects such as smoothness to keratin fibers such as hair.

Table 4 also shows that the foam according to the present invention can provide cosmetic effects to keratin fibers and that the cosmetic effects can be maintained after washing the keratin fibers. On the other hand, Table 4 shows that the conventional product can provide cosmetic effects to keratin fibers, but the cosmetic effects are reduced after washing the keratin fibers.

It is assumed that the DIC-gel in the foam according to the present invention can maintain the oil (a conditioning component) on hair due to hydrophobic interaction between the oil and the DIC-gel.

Examples 6-7 and Comparative Examples 3-12

(Preparation)

Foaming compositions according to Examples 6 and 7 were prepared by mixing the ingredients shown in Table 5 in the same manner as described for Example 1. The numerical values for the amounts of the ingredients shown in Table 5 are all based on "% by weight" as active raw materials.

Thus, it is understandable that the use of a cationic polysaccharide is necessary to stabilize a foam including a substantial amount of oil.

On the other hand, Table 5 shows that the use of the other cationic polymers (polyquaternium-6, polyquarternium-16, and polyquarternium-70) could not stabilize a foam including a substantial amount of oil (cf. Comparative Examples 3 to 6). It is assumed that the flexible chemical structure of these cationic polymers would easily make coacervates with phytic acid, but the coacervates would precipitate and could not stabilize the foam. In addition, it is difficult for flexible polymers to make micro-gels.

Also, Table 5 shows that the use of cationic polymers only (without any crosslinker such as phytic acid) cannot form stable foams (cf. Comparative Examples 7 to 12). In particular, based on the comparison with Examples 6 and 7 and Comparative Examples 7 and 8, respectively, it is clear that not only a cationic polysaccharide but also a crosslinker having three or more acid groups or salt thereof is necessary to provide a stable foam.

The invention claimed is:
1. A foaming composition, comprising:
   (a) at least one cationic polysaccharide;
   (b) at least one crosslinker having three or more acid groups or salt thereof;
   (c) at least one oil; and
   (d) at least one physiologically acceptable volatile medium,
   wherein the (a) cationic polysaccharide is selected from the group consisting of polyquaternium-4, polyquaternium-10, polyquaternium-24, polyquaternium-67, and a mixture thereof, the (b) crosslinker having three or more acid groups is selected from the group consisting of phytic acid, citric acid and a mixture thereof, the oil is selected from silicone oils,

TABLE 5

|  | Ex. 6 | Ex. 7 | Comp. Ex. 3 | Comp. Ex. 4 | Comp. Ex. 5 | Comp. Ex. 6 | Comp. Ex. 7 | Comp. Ex. 8 | Comp. Ex. 9 | Comp. Ex. 10 | Comp. Ex. 11 | Comp. Ex. 12 |
|---|---|---|---|---|---|---|---|---|---|---|---|---|
| Polyquaternium-67 | 0.5 | — | — | — | — | — | 0.5 | — | — | — | — | — |
| Polyquaternium-10 | — | 0.5 | — | — | — | — | — | 0.5 | — | — | — | — |
| Polyquaternium-6 | — | — | 0.5 | — | — | — | — | — | 0.5 | — | — | — |
| Polyquaternium-16 | — | — | — | 0.5 | — | — | — | — | — | 0.5 | — | — |
| Polyquaternium-70 | — | — | — | — | 0.5 | — | — | — | — | — | 0.5 | — |
| Polylysine | — | — | — | — | — | 0.5 | — | — | — | — | — | 0.5 |
| Phytic Acid | 0.20 | 0.20 | 0.20 | 0.20 | 0.20 | 0.20 | — | — | — | — | — | — |
| Water | qsp 100 | qsp 100 | qsp 100 | gsp 100 | gsp 100 | qsp 100 | qsp 100 | qsp 100 | qsp 100 | qsp 100 | qsp 100 | qsp 100 |
| Dimethicone | 30.00 | 30.00 | 30.00 | 30.00 | 30.00 | 30.00 | 30.00 | 30.00 | 30.00 | 30.00 | 30.00 | 30.0 |
| Stability of Foam | Stable | Stable | Unstable | Unstable | Unstable | Unstable | Unstable | Unstable | Unstable | Unstable | Unstable | Unstable |

(Evaluation)

45 g of each of the foaming compositions according to Examples 6-7 and 5 g of LPG (0.31 MPa) as propellant were charged into an aerosol bottle equipped with a dispenser. After shaking the aerosol bottle well, the dispenser was activated to discharge the foaming composition as a foam. The stability of the foam was visually observed and evaluated in accordance with the following criteria.

Stable: The foam was maintained for more than 1 minute
Unstable: The foam was broken within 1 minute The results of the evaluation are shown in Table 5.

Table 5 shows that the DIC gel comprising polyquaternium-67 or polyquaternium-10 was able to stabilize a foam including a substantial amount of oil (cf. Examples 6 and 7).

the amount of the (a) cationic polysaccharide(s) in the composition is from 0.01% to 20% by weight, relative to the total weight of the composition, the amount of the (b) crosslinker(s) having three or more acid groups or salt(s) thereof in the composition is from 0.001% to 15% by weight, relative to the total weight of the composition, and the amount of the (c) oil(s) in the composition is 10% by weight or more, relative to the total weight of the composition.

2. The composition according to claim 1, wherein the amount of the (d) physiologically acceptable volatile medium(s) in the composition is from 50% to 90% by weight, relative to the total weight of the composition.

3. The composition according to claim 1, wherein the composition further comprises (e) at least one anionic polymer.

4. The composition according to claim 1, wherein the composition is a cosmetic composition.

5. The composition according to claim 1, wherein the composition further comprises at least one gas and is in the form of a foam.

6. A cosmetic process for a keratin substrate, comprising the steps of:
    foaming the composition according to claim 1 to prepare a foam; and
    applying the foam to the keratin substrate.

7. A foaming product comprising:
    at least one container comprising the composition according to claim 1; and
    at least one dispenser, wherein the dispenser is capable of discharging the composition in the form of a foam.

8. The foaming product according to claim 7, wherein the container further comprises at least one propellant.

9. The foaming product according to claim 7, further comprising at least one pump which is connected to the container and the dispenser, wherein the pump is capable of mixing the composition with at least one gas to prepare a foam and of conveying the foam to the dispenser.

10. The composition according to claim 1, wherein the amount of the (a) cationic polysaccharide(s) in the composition is from 0.1% to 15% by weight, relative to the total weight of the composition.

11. The composition according to claim 1, wherein the amount of the (a) cationic polysaccharide(s) in the composition is from 0.5% to 10% by weight, relative to the total weight of the composition.

12. The composition according to claim 1, wherein the amount of the (b) crosslinker(s) having three or more acid groups or salt(s) thereof in the composition is from 0.05% to 10% by weight, relative to the total weight of the composition.

13. The composition according to claim 1, wherein the amount of the (b) crosslinker(s) having three or more acid groups or salt(s) thereof in the composition is from 0.1% to 5% by weight, relative to the total weight of the composition.

14. The composition according to claim 1, wherein the amount of the (c) oil(s) in the composition is 15% by weight or more, relative to the total weight of the composition.

15. The composition according to claim 1, wherein the amount of the (c) oil(s) in the composition is 20% by weight or more, relative to the total weight of the composition.

16. The composition according to claim 1, wherein the amount of the (c) oil(s) in the composition is less than 45% by weight, relative to the total weight of the composition.

17. The composition according to claim 1, wherein the amount of the (c) oil(s) in the composition is less than 40% by weight, relative to the total weight of the composition.

18. The composition according to claim 1, wherein the amount of the (d) physiologically acceptable volatile medium(s), in the composition is from 55% to 85% by weight, relative to the total weight of the composition.

19. The composition according to claim 1, wherein the amount of the (d) physiologically acceptable volatile medium(s), in the composition is from 60% to 80% by weight, relative to the total weight of the composition.

20. The composition according to claim 1, wherein the (d) physiologically acceptable volatile medium is water.

* * * * *